(12) United States Patent
Zannis et al.

(10) Patent No.: US 8,632,600 B2
(45) Date of Patent: Jan. 21, 2014

(54) PROSTHESIS WITH MODULAR EXTENSIONS

(75) Inventors: Anthony D. Zannis, Fort Wayne, IN (US); Daren L. Deffenbaugh, Winona Lake, IN (US)

(73) Assignee: Depuy (Ireland), Cork (IE)

( * ) Notice: Subject to any disclaimer, the term of this patent is extended or adjusted under 35 U.S.C. 154(b) by 77 days.

(21) Appl. No.: 12/904,614

(22) Filed: Oct. 14, 2010

(65) Prior Publication Data
US 2011/0029090 A1 Feb. 3, 2011

Related U.S. Application Data

(63) Continuation-in-part of application No. 11/860,833, filed on Sep. 25, 2007, now Pat. No. 8,470,047, and a continuation-in-part of application No. 12/620,034, filed on Nov. 17, 2009, now Pat. No. 8,128,703.

(60) Provisional application No. 61/256,527, filed on Oct. 3, 2009.

(51) Int. Cl.
*A61F 2/38* (2006.01)

(52) U.S. Cl.
USPC .................................................. 623/20.17

(58) Field of Classification Search
USPC .......... 623/20.32–20.36, 20.14, 20.15, 20.21, 623/20.16, 20.29, 20.31, 23.6–23.63, 623/23.72–23.76
See application file for complete search history.

(56) References Cited

U.S. PATENT DOCUMENTS

| | | | |
|---|---|---|---|
| 3,855,638 A | | 12/1974 | Pilliar |
| D248,771 S | * | 8/1978 | Groth et al. .................. D24/155 |
| 4,156,943 A | | 6/1979 | Collier |
| 4,206,516 A | | 6/1980 | Pilliar |
| 4,257,129 A | | 3/1981 | Volz |
| 4,479,271 A | | 10/1984 | Bolesky et al. |
| 4,550,448 A | | 11/1985 | Kenna |
| 4,612,160 A | | 9/1986 | Donlevy |
| 4,673,407 A | | 6/1987 | Martin |
| 4,714,474 A | | 12/1987 | Brooks, Jr. |
| 4,795,468 A | | 1/1989 | Hodorek |
| 4,822,362 A | | 4/1989 | Walker |
| 4,838,891 A | | 6/1989 | Branemark et al. |

(Continued)

FOREIGN PATENT DOCUMENTS

| | | | |
|---|---|---|---|
| EP | 0495340 A1 | 12/1991 | |
| EP | 0063632 A1 | 2/1995 | |

(Continued)

OTHER PUBLICATIONS

Carl Zeiss, Zeiss Surfcomm 5000—"Contour and Surface Measuring Machines," 2005, 16 Pages.

(Continued)

*Primary Examiner* — Alvin J. Stewart

(57) ABSTRACT

A joint prosthesis system has two implant components and a bearing. One of the implant components has an articulation surface for articulation with the bearing. The other implant component has a mounting surface for supporting the bearing. At least one of the first and second components includes a recess and a stud in the recess. The joint prosthesis also includes an extension mounted on the stud and extending out from the bone-engaging surface to an end. Part of the extension is received in the recess.

6 Claims, 17 Drawing Sheets

(56) References Cited

U.S. PATENT DOCUMENTS

| | | | |
|---|---|---|---|
| 4,938,769 A * | 7/1990 | Shaw | 623/20.15 |
| 4,944,757 A * | 7/1990 | Martinez et al. | 623/20.15 |
| 4,944,760 A | 7/1990 | Kenna | |
| 4,950,298 A | 8/1990 | Gustilo | |
| 4,954,170 A | 9/1990 | Fey | |
| 4,963,152 A | 10/1990 | Hofmann | |
| 4,969,907 A | 11/1990 | Koch | |
| 4,990,163 A | 2/1991 | Ducheyne et al. | |
| 5,019,103 A | 5/1991 | Van Zile | |
| 5,080,674 A | 1/1992 | Jacobs et al. | |
| 5,080,675 A | 1/1992 | Lawes | |
| 5,104,410 A | 4/1992 | Chowdhary | |
| 5,171,283 A | 12/1992 | Pappas | |
| 5,194,066 A * | 3/1993 | Van Zile | 623/20.15 |
| 5,201,766 A | 4/1993 | Georgette | |
| 5,201,768 A * | 4/1993 | Caspari et al. | 623/20.32 |
| 5,258,044 A | 11/1993 | Lee | |
| 5,271,737 A | 12/1993 | Baldwin | |
| 5,282,861 A | 2/1994 | Kaplan | |
| 5,308,556 A | 5/1994 | Bagley | |
| 5,309,639 A | 5/1994 | Lee | |
| 5,344,460 A | 9/1994 | Turanyi | |
| 5,344,494 A | 9/1994 | Davidson | |
| 5,368,881 A | 11/1994 | Kelman | |
| 5,370,699 A | 12/1994 | Hood | |
| 5,387,240 A | 2/1995 | Pottenger | |
| 5,405,396 A | 4/1995 | Heldreth | |
| 5,413,604 A | 5/1995 | Hodge | |
| 5,454,365 A | 10/1995 | Bonutti | |
| 5,480,444 A | 1/1996 | Incavo | |
| 5,480,445 A * | 1/1996 | Burkinshaw | 623/20.32 |
| 5,480,446 A | 1/1996 | Goodfellow | |
| 5,571,187 A | 11/1996 | Devanathan | |
| 5,605,491 A | 2/1997 | Yam | |
| 5,609,639 A | 3/1997 | Walker | |
| 5,609,641 A * | 3/1997 | Johnson et al. | 623/20.32 |
| 5,658,333 A | 8/1997 | Kelman | |
| 5,658,341 A * | 8/1997 | Delfosse | 623/20.32 |
| 5,658,342 A | 8/1997 | Draganich | |
| 5,702,447 A | 12/1997 | Walch | |
| 5,702,464 A | 12/1997 | Lackey | |
| 5,728,748 A | 3/1998 | Sun | |
| 5,755,800 A * | 5/1998 | O'Neil et al. | 623/20.16 |
| 5,755,801 A | 5/1998 | Walker | |
| 5,765,095 A | 6/1998 | Flak | |
| 5,766,257 A | 6/1998 | Goodman | |
| 5,824,103 A | 10/1998 | Williams | |
| 5,847,012 A | 12/1998 | Shalaby | |
| 5,868,797 A * | 2/1999 | Pappas et al. | 623/20.32 |
| 5,871,545 A | 2/1999 | Goodfellow | |
| 5,871,546 A | 2/1999 | Colleran | |
| 5,879,387 A | 3/1999 | Jones | |
| 5,879,394 A | 3/1999 | Ashby | |
| 5,879,400 A | 3/1999 | Merrill | |
| 5,902,315 A | 5/1999 | DuBois | |
| 5,957,979 A | 9/1999 | Beckman | |
| 5,964,808 A | 10/1999 | Blaha | |
| 5,984,969 A | 11/1999 | Matthews | |
| 5,989,027 A | 11/1999 | Wagner | |
| 6,005,018 A | 12/1999 | Cicierega | |
| 6,017,975 A | 1/2000 | Saum | |
| 6,039,764 A * | 3/2000 | Pottenger et al. | 623/20.32 |
| 6,042,780 A | 3/2000 | Huang | |
| 6,059,949 A | 5/2000 | Gal-Or et al. | |
| 6,068,658 A | 5/2000 | Insall | |
| 6,090,144 A | 7/2000 | Letot | |
| 6,117,175 A * | 9/2000 | Bosredon | 623/20.15 |
| 6,123,728 A | 9/2000 | Brosnahan | |
| 6,126,692 A | 10/2000 | Robie | |
| 6,135,857 A | 10/2000 | Shaw | |
| 6,139,581 A | 10/2000 | Engh | |
| 6,162,254 A | 12/2000 | Timoteo | |
| 6,179,876 B1 * | 1/2001 | Stamper et al. | 623/18.11 |
| 6,183,519 B1 | 2/2001 | Bonnin | |
| 6,210,444 B1 | 4/2001 | Webster | |
| 6,210,445 B1 | 4/2001 | Zawadzki | |
| 6,217,618 B1 | 4/2001 | Hileman | |
| 6,228,900 B1 | 5/2001 | Shen | |
| 6,238,434 B1 | 5/2001 | Pappas | |
| 6,242,507 B1 | 6/2001 | Saum | |
| 6,245,276 B1 | 6/2001 | McNulty | |
| 6,258,127 B1 | 7/2001 | Schmotzer | |
| 6,280,476 B1 | 8/2001 | Metzger et al. | |
| 6,281,264 B1 | 8/2001 | Salovey | |
| 6,299,646 B1 | 10/2001 | Chambat | |
| 6,312,473 B1 | 11/2001 | Oshida | |
| 6,316,158 B1 | 11/2001 | Saum | |
| 6,319,283 B1 | 11/2001 | Insall | |
| 6,361,564 B1 | 3/2002 | Marceaux | |
| 6,379,388 B1 | 4/2002 | Ensign | |
| 6,443,991 B1 | 9/2002 | Running | |
| 6,506,215 B1 | 1/2003 | Letot | |
| 6,506,216 B1 | 1/2003 | McCue et al. | |
| 6,524,522 B2 | 2/2003 | Vaidyanathan | |
| 6,569,202 B2 | 5/2003 | Whiteside | |
| 6,620,198 B2 * | 9/2003 | Burstein et al. | 623/20.28 |
| 6,623,526 B1 | 9/2003 | Lloyd | |
| 6,626,950 B2 | 9/2003 | Brown | |
| 6,660,039 B1 | 12/2003 | Evans | |
| 6,797,006 B2 | 9/2004 | Hodorek | |
| 6,869,448 B2 | 3/2005 | Tuke | |
| 6,896,702 B2 * | 5/2005 | Collazo | 623/20.16 |
| 6,923,832 B1 | 8/2005 | Sharkey | |
| 6,939,380 B2 | 9/2005 | Guzman | |
| 6,953,479 B2 * | 10/2005 | Carson et al. | 623/20.15 |
| 6,972,039 B2 | 12/2005 | Metzger | |
| 6,986,791 B1 | 1/2006 | Metzger | |
| 7,011,687 B2 | 3/2006 | Deffenbaugh | |
| 7,025,790 B2 | 4/2006 | Parks | |
| 7,094,259 B2 | 8/2006 | Tarabichi | |
| 7,101,401 B2 | 9/2006 | Brack | |
| 7,175,665 B2 | 2/2007 | German | |
| 7,179,295 B2 * | 2/2007 | Kovacevic | 623/17.15 |
| 7,208,013 B1 | 4/2007 | Bonutti | |
| 7,208,222 B2 * | 4/2007 | Rolfe et al. | 428/304.4 |
| 7,294,149 B2 | 11/2007 | Hozack | |
| 7,344,460 B2 | 3/2008 | Gait | |
| 7,462,199 B2 * | 12/2008 | Justin et al. | 623/20.34 |
| 7,534,270 B2 | 5/2009 | Ball | |
| 7,628,817 B1 | 12/2009 | Axelson, Jr. | |
| 7,628,818 B2 | 12/2009 | Hazebrouck | |
| 7,753,960 B2 | 7/2010 | Cipolletti | |
| 7,771,484 B2 | 8/2010 | Campbell | |
| 8,070,821 B2 | 12/2011 | Roger | |
| 8,100,981 B2 * | 1/2012 | Clark et al. | 623/20.32 |
| 8,105,387 B2 * | 1/2012 | Barnett et al. | 623/20.32 |
| 8,128,703 B2 | 3/2012 | Hazebrouck | |
| 8,163,027 B2 * | 4/2012 | Rhodes et al. | 623/20.34 |
| 2001/0047211 A1 * | 11/2001 | Leclercq et al. | 623/20.32 |
| 2003/0014122 A1 | 1/2003 | Whiteside | |
| 2003/0044301 A1 | 3/2003 | Lefebvre | |
| 2003/0075013 A1 | 4/2003 | Grohowski | |
| 2003/0139817 A1 | 7/2003 | Tuke et al. | |
| 2003/0171820 A1 | 9/2003 | Wilshaw | |
| 2003/0212161 A1 | 11/2003 | McKellop | |
| 2004/0015170 A1 | 1/2004 | Tallarida | |
| 2004/0030397 A1 * | 2/2004 | Collazo | 623/20.32 |
| 2004/0049284 A1 * | 3/2004 | German et al. | 623/20.15 |
| 2004/0186583 A1 | 9/2004 | Keller | |
| 2004/0186585 A1 | 9/2004 | Feiwell | |
| 2004/0215345 A1 | 10/2004 | Perrone | |
| 2005/0021147 A1 | 1/2005 | Tarabichi | |
| 2005/0055102 A1 | 3/2005 | Tornier et al. | |
| 2005/0069629 A1 | 3/2005 | Becker et al. | |
| 2005/0100578 A1 | 5/2005 | Schmid | |
| 2005/0107884 A1 * | 5/2005 | Johnson et al. | 623/20.15 |
| 2005/0123672 A1 | 6/2005 | Justin et al. | |
| 2005/0203631 A1 | 9/2005 | Daniels et al. | |
| 2005/0209702 A1 | 9/2005 | Todd | |
| 2005/0249625 A1 | 11/2005 | Bram | |
| 2006/0002810 A1 | 1/2006 | Grohowski | |
| 2006/0036329 A1 | 2/2006 | Webster et al. | |
| 2006/0052875 A1 | 3/2006 | Bernero | |
| 2006/0100714 A1 | 5/2006 | Ensign | |

(56) References Cited

U.S. PATENT DOCUMENTS

| | | | |
|---|---|---|---|
| 2006/0163774 A1 | 7/2006 | Abels et al. | |
| 2006/0178749 A1 | 8/2006 | Pendleton et al. | |
| 2006/0195195 A1 | 8/2006 | Burstein et al. | |
| 2006/0228247 A1 | 10/2006 | Grohowski | |
| 2006/0231402 A1 | 10/2006 | Clasen et al. | |
| 2006/0235537 A1* | 10/2006 | Kuczynski et al. | 623/20.3 |
| 2006/0241781 A1 | 10/2006 | Brown | |
| 2006/0257358 A1 | 11/2006 | Wen | |
| 2006/0271191 A1 | 11/2006 | Hermansson | |
| 2007/0010890 A1* | 1/2007 | Collazo | 623/20.15 |
| 2007/0073409 A1 | 3/2007 | Cooney | |
| 2007/0078521 A1 | 4/2007 | Overholser et al. | |
| 2007/0129809 A1 | 6/2007 | Meridew | |
| 2007/0179628 A1* | 8/2007 | Rochetin | 623/20.34 |
| 2007/0196230 A1 | 8/2007 | Hamman | |
| 2007/0203582 A1 | 8/2007 | Campbell | |
| 2007/0255412 A1 | 11/2007 | Hajaj | |
| 2007/0287027 A1 | 12/2007 | Justin | |
| 2007/0293647 A1 | 12/2007 | McKellop | |
| 2008/0021567 A1 | 1/2008 | Meulink | |
| 2008/0091271 A1* | 4/2008 | Bonitati et al. | 623/20.34 |
| 2008/0091272 A1 | 4/2008 | Aram | |
| 2008/0161927 A1 | 7/2008 | Savage et al. | |
| 2008/0188855 A1* | 8/2008 | Brown et al. | 606/88 |
| 2008/0199720 A1 | 8/2008 | Liu | |
| 2008/0206297 A1 | 8/2008 | Roeder et al. | |
| 2009/0082873 A1 | 3/2009 | Hazebrouck | |
| 2009/0084491 A1 | 4/2009 | Uthgenannt et al. | |
| 2009/0088859 A1 | 4/2009 | Hazebrouck et al. | |
| 2009/0100190 A1 | 4/2009 | Besombe | |
| 2009/0125115 A1 | 5/2009 | Popoola | |
| 2009/0182433 A1 | 7/2009 | Reiley | |
| 2009/0192610 A1 | 7/2009 | Case et al. | |
| 2009/0292365 A1 | 11/2009 | Smith | |
| 2009/0326674 A1 | 12/2009 | Liu | |
| 2010/0042225 A1 | 2/2010 | Shur | |
| 2010/0063594 A1 | 3/2010 | Hazebrouck et al. | |
| 2010/0094429 A1* | 4/2010 | Otto | 623/20.14 |
| 2010/0098574 A1 | 4/2010 | Liu | |
| 2010/0100191 A1* | 4/2010 | May et al. | 623/20.34 |
| 2010/0262144 A1 | 10/2010 | Kelman | |
| 2011/0009974 A1 | 1/2011 | Blaylock | |
| 2011/0071642 A1* | 3/2011 | Moussa | 623/20.14 |

FOREIGN PATENT DOCUMENTS

| | | |
|---|---|---|
| EP | 1421918 B1 | 11/2003 |
| EP | 1923079 A1 | 5/2008 |
| FR | 2653992 A1 | 5/1991 |
| FR | 2780636 A1 | 1/2000 |
| GB | 1065354 A | 4/1967 |
| GB | 2293109 A1 | 3/1996 |
| WO | WO 9966864 A1 | 12/1999 |
| WO | WO 03039609 A1 | 5/2003 |
| WO | WO 2006014294 A1 | 2/2006 |
| WO | WO 2009046212 A2 | 4/2009 |
| WO | WO 2009128943 A2 | 10/2009 |

OTHER PUBLICATIONS

German, Randall "Powder Injection Molding," ASM Handbook, vol. 7, (1998), pp. 355-364.

Phelly Materials, Inc. "Hybride and Dehydride CP Ti and Ti-6A1-4V Powders," 2007, 1 Page.

Phelly Materials, Inc., "Pure Metal Powder," 2007, 1 Page.

International Standard ISO 4287:1997; Geometrical Product Specifications (GPS)—Surface Texture: Profile Method—Terms, Definitions and Surface Texture Parameters, Technical Corrigendum 2, 2005, 2 Pages.

International Standard ISO 4287:1997; Geometrical Product Specifications (GPS)—Surface Texture: Profile Method—Terms, Definitions and Surface Texture Parameters, Technical Corrigendum 1, 1998, 2 Pages.

International Standard ISO 4287:1997; Geometrical Product Specifications (GPS)—Surface Texture: Profile Method—Terms, Definitions and Surface Texture Parameters, 1997, 36 Pages.

Biomet, Vanguard® Mono-Lock™ Tibial System, Patented Convertible Tibial Bearing Technology, 2009, 2 Pages.

Depuy Inc., "AMK Total Knee System Product Brochure", 1996, 8 pages (7628818).

Depuy Orthopaedics, Inc., "AMK Total Knee System Legend II Surgical Technique", 1998, 30 pages (7628818).

Depuy PFC Sigma RP, "PFC Sigma Knee System With Rotating Platform Technical Monograph", 1999, 0611-29-050 (Rev. 3), 70 Pages.

Sigma, "Fixed Bearing Knees—Function With Wear Resistance", 2010, 0612-65-508 (Rev. 1), 20 Pages.

Johnson & Johnson Orthopaedics, "Primary Cruciate-Retaining & Cruciate-Substituting Procedure", Reference Guide for Use With PFC Sigma Knee Systems, 1998 (11-860833).

European Search Report for European Patent Application No. 08164944.4-2310-2042131, Mar. 16, 2009, 12 pages (11-860833).

European Search Report for EP09170648 Dated Mar. 1, 2010.

Partial European Search Report for EP09170648 Dated Jan. 31, 2010.

European Search Report for European Patent Application No. 08253140.1-2310, Dec. 23, 2008, 8 Pages.

European Search Report for European Patent Application No. 10188963.2-2310, Mar. 1, 2011, 7 Pages.

European Search Report for European Patent Application No. 10188962.4-2310, Mar. 2, 2011, 8 Pages.

Taking a Peek At Material Options for Orthopedics, Amy Kinbrum, Advantage Business Media, 2008, 6 Pages.

Zimmer, Trabecular Metal Monoblock Tibial Components, An Optimal Combination of Material and Design, www.zimmer.com, 2009, 3 Pages.

Zimmer, Trabecular Metal™ Technology, www.zimmer.com, 2009, 4 Pages.

Zimmer Nexgen Trabecular Metal Tibial Tray, The Best Thing Next to Bone, 97-5954-001-00, 2007, 4 Pages.

* cited by examiner

PROSTHESIS WITH MODULAR EXTENSIONS

CROSS-REFERENCE TO RELATED APPLICATIONS

Priority is claimed to the following application: U.S. Provisional Patent Application Ser. No. 61/256,527 entitled, "PROSTHESIS WITH MODULAR EXTENSIONS," filed on Oct. 30, 2010 by Anthony D. Zannis and Daren L. Deffenbaugh. The present application is also a continuation-in-part of the following U.S. patent applications, the disclosures of which are incorporated by reference herein in their entireties: U.S. Pat. No. 8,470,047 (U.S. patent application Ser. No. 11/860,833) filed on Sep. 25, 2007 and entitled "Fixed-Bearing Knee Prosthesis" and U.S. Pat. No. 8,128,703 (U.S. patent application Ser. No. 12/620,034) filed on Nov. 17, 2009 and entitled "Fixed-Bearing Knee Prosthesis Having Interchangeable Components".

TECHNICAL FIELD

The present disclosure relates generally to an implantable orthopaedic prosthesis, and more particularly to an implantable prosthesis having a bearing component and another component supporting the bearing component.

BACKGROUND

During the lifetime of a patient, it may be necessary to perform a joint replacement procedure on the patient as a result of, for example, disease or trauma. The joint replacement procedure may involve the use of a prosthesis that is implanted into one or more of the patient's bones. In the case of a knee replacement procedure, a tibial tray is implanted into the patient's tibia. A bearing is then secured to the tibial tray. The condyle surfaces of a replacement femoral component bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

In contrast, in a mobile-bearing type of knee prosthesis, the bearing can move relative to the tibial tray. Mobile-bearing knee prostheses include so-called "rotating platform" knee prostheses, wherein the bearing can rotate about a longitudinal axis on the tibial tray.

Tibial trays are commonly made of a biocompatible metal, such as a cobalt chrome alloy or a titanium alloy.

For both fixed and mobile-bearing knee prostheses, the tibial trays may be designed to be cemented into place on the patient's tibia or alternatively may be designed for cementless fixation. Cemented fixation relies on mechanical bonds between the tibial tray and the cement as well as between the cement and the bone. Cementless implants generally have surface features that are conducive to bone ingrowth into the implant component and rely to a substantial part on this bony ingrowth for secondary fixation; primary fixation is achieved through the mechanical fit of the implant and the prepared bone.

Tibial components of both fixed and mobile-bearing and cemented and cementless knee arthroplasty systems are commonly modular components, comprising a tibial tray and a polymeric bearing carried by the tibial tray. The tibial trays commonly include features extending distally, such as pegs or stems. These extensions penetrate below the surface of the tibial plateau and stabilize the tibial tray component against movement. In cementless tibial implants, the outer surfaces of these extensions are typically porous to allow for bone ingrowth. For example, in the Zimmer Trabecular Metal Monoblock tibial trays, pegs with flat distal surfaces and hexagonal axial surfaces are formed completely of a porous metal. In such trays, bone ingrowth is likely to occur along all surfaces of the pegs, including the distal surfaces.

Femoral components of such knee prosthesis systems are also designed for either cemented or cementless fixation. For cemented fixation, the femoral component typically includes recesses or cement pockets. For cementless fixation, the femoral component is designed for primary fixation through a press-fit, and includes porous bone-engaging surfaces suitable for bone ingrowth. Both designs may include pegs designed to extend into prepared holes in the femur for stabilization of the implant.

On occasion, the primary knee prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary knee prosthesis (or parts of it) is removed and replaced with components of a revision prosthetic system.

When the tibial or femoral implant includes extensions (such as pegs or stems) that extend into the natural bone, a revision surgery usually requires a large resection of the bone in order to dislodge the extensions from the bone. This large resection not only complicates the surgery, it also requires removal of more of the patient's natural bone than is desirable. This removal of additional bone may further compromise the bone, increase the risk of onset of bone pathologies or abnormalities, or reduce the available healthy bone for fixation of the revision implant. Moreover, the large resection usually means that a larger orthopaedic implant is necessary to fill the space and restore the joint component to its expected geometry.

This difficulty in dislodging the primary implant components from the bones is worsened by the fact that bone also grows into the extensions. Severing these connections may be problematic since not all of these areas are easily accessible without resecting large amounts of bone.

Similar issues may be presented in other types of joint prostheses.

SUMMARY

The present invention addresses the need for a prosthesis with a modular implant component suitable for cementless fixation that can be removed more readily from the bone in revision surgery to conserve native bone. In addition, a method of making such a prosthesis is disclosed, as well as a surgical method for removing such a prosthesis. While the illustrated embodiments of the invention address all of these needs, it should be understood that the scope of the invention as defined by the claims may include prostheses that address one or more of these needs. It should also be understood that various aspects of the present invention provide other additional advantages, as set forth more fully below. In addition, it should be understood that the principles of the present invention may be applied to knee prostheses as well as other joint prostheses, such as, for example, an ankle prosthesis.

In one aspect, the present invention provides a joint prosthesis comprising a first component, a bearing and a second component. The first component has an articulation surface and an opposite bone-engaging surface. The bearing has an articulation surface shaped to bear against the articulation surface of the first component and an opposite surface. The second component has a mounting surface and an opposite bone-engaging surface. At least one of the first and second components includes a recess and a stud in the recess. The joint prosthesis also includes an extension mounted on the stud and extending out from the bone-engaging surface to an end. The extension has an outer surface between the end and the bone-engaging surface. A part of the extension is received in the recess.

In an exemplary embodiment, the stud is threaded and the extension includes a threaded bore engaging the stud.

In another exemplary embodiment, the stud defines a Morse taper post and the extension includes a Morse taper bore engaging the stud.

In an exemplary embodiment, the first component includes a solid metal portion and the recess and stud are part of the solid metal portion. The first component may further include a porous metal portion that defines the bone-engaging surface of the first component.

In an exemplary embodiment, the porous metal portion and the extension comprise titanium metal foam and the solid metal portion comprises a titanium alloy.

In an exemplary embodiment, the porous metal portion, solid metal portion and extension are bonded together through sintering and the extension and the porous metal portion meet at a junction. The junction of the extension and the porous metal portion may comprise titanium metal foam.

In an exemplary embodiment, the joint prosthesis may include a plurality of extensions. The first component may include a plurality of spaced recesses and a plurality of spaced studs, each stud within one recess and each stud having an end. Each extension is mounted on a stud and bonded to the porous metal portion and solid metal portion through sintering. Each extension meets the porous metal portion at a junction. These junctions lie in a plane. The ends of the studs do not extend beyond the plane of the junctions.

In an exemplary embodiment, the joint prosthesis is a knee prosthesis, the first component comprises a distal femoral component and the second component comprises a proximal tibial tray.

In another exemplary embodiment, the joint prosthesis is an ankle prosthesis and the first component comprises a distal tibial component.

In another exemplary embodiment, the second component includes a solid metal portion and the recess and stud are part of the solid metal portion.

In another exemplary embodiment, the second component includes a porous metal portion and the bone-engaging surface is part of the porous metal portion. The porous metal portion and the extension may comprise titanium metal foam and the solid metal portion may comprise a titanium alloy. The porous metal portion, solid metal portion and extension may be bonded together through sintering and wherein the extension and the porous metal portion meet at a junction. The junction of the extension and the porous metal portion may comprise titanium metal foam.

In an exemplary embodiment, the joint prosthesis includes a plurality of extensions and the second component includes a plurality of spaced recesses and a plurality of spaced studs, each stud being within one recess and having an end. Each extension is mounted on a stud and bonded to the porous metal portion and solid metal portion through sintering. Each extension meets the porous metal portion at a junction. The junctions lie in a plane and the ends of the studs do not extend beyond the plane of the junctions.

In an exemplary embodiment, the joint prosthesis is a knee prosthesis, the first component comprises a distal femoral component and the second component comprises a proximal tibial tray.

In another aspect, the present invention provides a joint prosthesis comprising a first metal component, a bearing and a second metal component. The first metal component has a solid metal articulation surface and a bone-engaging surface. The bearing has an articulation surface shaped to bear against the articulation surface of the first metal component and an opposite surface. The second metal component has a solid metal mounting surface and an opposite bone-engaging surface. The joint prosthesis also has an extension extending out from a junction with the bone-engaging surface of one of the metal components to an exposed end. The extension has an exposed outer surface and is configured for stabilizing the metal component when implanted in a bone of a patient. The solid metal portion of the metal component from which the extension extends comprises titanium and the exposed outer surface of the extension comprises a different form of titanium.

In one embodiment, the first metal component and second metal component include a titanium alloy and the extension comprises commercially pure titanium. More particularly, the exposed outer surface of the extension comprises porous titanium.

In an exemplary embodiment, the extension comprises titanium foam. The extension may have a thickness at the junction and the extension may consists of titanium foam across the entire thickness of the extension at the junction. In an exemplary embodiment, at least part of the extension has a void space of at least 65% by volume.

In another exemplary embodiment, the exposed outer surface of the extension at the end of the extension has a different roughness than at least a part of the exposed outer surface of the extension between the end and the junction.

In another exemplary embodiment, the extension is selected from the group consisting of a peg and a stem.

In another exemplary embodiment, the bone-engaging surface of at least one of the metal components comprises porous metal. More particularly, the porous metal may comprise commercially pure titanium.

In an exemplary embodiment, the prosthesis is an ankle prosthesis. The first metal component comprises a distal tibial component and the extension extends out from the bone-engaging surface of the distal tibial component.

In another exemplary embodiment, the joint prosthesis is a knee prosthesis. The first metal component is a distal femoral component configured to replace the distal end of the femur and the second metal component is a tibial tray configured to replace the proximal end of the tibia. In this embodiment, the mounting surface of the tibial tray may comprise solid titanium alloy and the extension may comprise a foam of commercially pure titanium; the solid titanium alloy may extending from the mounting surface toward the bone-engaging surface and the extension may be bonded to the solid titanium alloy of the tibial tray by sintering. In this embodiment, the bone-engaging surface of the tibial tray may comprise commercially pure titanium foam bonded to the solid titanium alloy of the tibial tray by sintering. The articulating surface of the femoral component may also comprise solid titanium alloy and the extension may comprise of foam of commercially pure titanium bonded to the solid titanium alloy by sintering; in this embodiment, the solid titanium alloy extends from the articulating surface toward the bone-engaging surface and the bone-engaging surface of the femoral component may comprise commercially pure titanium foam bonded to the solid titanium alloy of the femoral component by sintering.

In another aspect, the present invention provides a joint prosthesis comprising a first metal component, a bearing and a second metal component. The first metal component has a solid metal articulation surface and a bone-engaging surface. The bearing has an articulation surface shaped to bear against the articulation surface of the metal component and an opposite surface. The second metal component has a solid metal mounting surface and a bone-engaging surface. The joint prosthesis also has an extension extending out from the bone-engaging surface of at least one of the metal components. The extension is configured for stabilizing the metal component when implanted in a bone of a patient. In addition, the extension has an exposed end spaced from the bone-engaging surface and joins the bone-engaging surface at a junction. The extension has an outer surface between the junction and the end of the extension. The texture of the outer surface of the extension at the end is different from the texture of the outer surface of the extension between the end and the junction.

In an exemplary embodiment, the outer surface of the extension has a coefficient of static friction at the end that is less than the coefficient of static friction between the end and the junction.

In another aspect, the present invention provides a joint prosthesis comprising a first metal component, a bearing and a second metal component. The first metal component has a solid metal articulation surface and a bone-engaging surface. The bearing has an articulation surface shaped to bear against the articulation surface of the metal component and an opposite surface. The second metal component has a solid metal mounting surface and an opposite bone-engaging surface. The joint prosthesis also includes an extension extending out from a junction at the bone-engaging surface of one of the metal components to an exposed end. The extension is configured for stabilizing the metal component when implanted in a bone of a patient. The extension has a thickness at the junction and consists of porous metal across the entire thickness of the extension at the junction.

In another aspect, the present invention provides a method of making an orthopaedic implant. The method includes the steps of providing a solid metal base and a porous metal extension to be assembled with the solid metal base. The solid metal base has a first surface and a second surface opposite to the first surface. The porous metal extension and the second surface of the solid metal base include complementary mounting structures for assembling the porous metal extension and the solid metal base. The method includes the step of assembling the porous metal extension and the base followed by sintering the assembly of the porous metal extension and the base to bond the porous metal extension to the base.

The method may also include the step of providing a porous metal preform having a shape different than the shape of the porous metal extension.

If such a preform is provided, the method further comprises the steps of placing the porous metal preform against the second surface of the base and sintering the preform to the base.

The porous metal extension and the porous metal base may comprise an integral component and the steps of assembling the porous metal extension and the base and placing the porous metal preform against the second surface of the base are performed simultaneously.

Alternatively, the porous metal extension and the porous metal base may comprise discrete components and the steps of assembling the porous metal extension and the base and placing the porous metal preform against the second surface of the base are performed separately.

In one embodiment of the method of the present invention, the porous metal extension has two ends. The mounting structure of the porous metal extension is at one end and is surrounded by porous metal. The opposite end of the porous metal extension has different surface characteristics compared to the porous metal surrounding the mounting structure.

The different surface characteristics of the opposite end of the extension may be achieved by treating the opposite end of the porous metal extension to adjust its surface characteristics.

Treatment of the opposite end of the porous metal extension may comprise machining, milling or polishing.

Alternatively, treatment of the opposite end of the porous metal extension may comprise bonding the porous metal to another material. The other material may comprise solid metal or, in the alternative, polyetheretherketone (PEEK).

In another aspect, the present invention provides a method of removing an orthopaedic implant from a bone. The orthopaedic implant comprises a body having a bone-engaging surface engaging the bone at an interface and an extension extending deeper into the bone. The method comprises the step of introducing a saw blade between the bone-engaging surface of the body and the bone at the interface to separate the bone-engaging surface from the bone and sawing through the extension to separate the extension from the body. The method may further comprise the step of sawing around the extension.

BRIEF DESCRIPTION OF THE DRAWINGS

The detailed description particularly refers to the following figures, in which.

DETAILED DESCRIPTION

Figure 1:
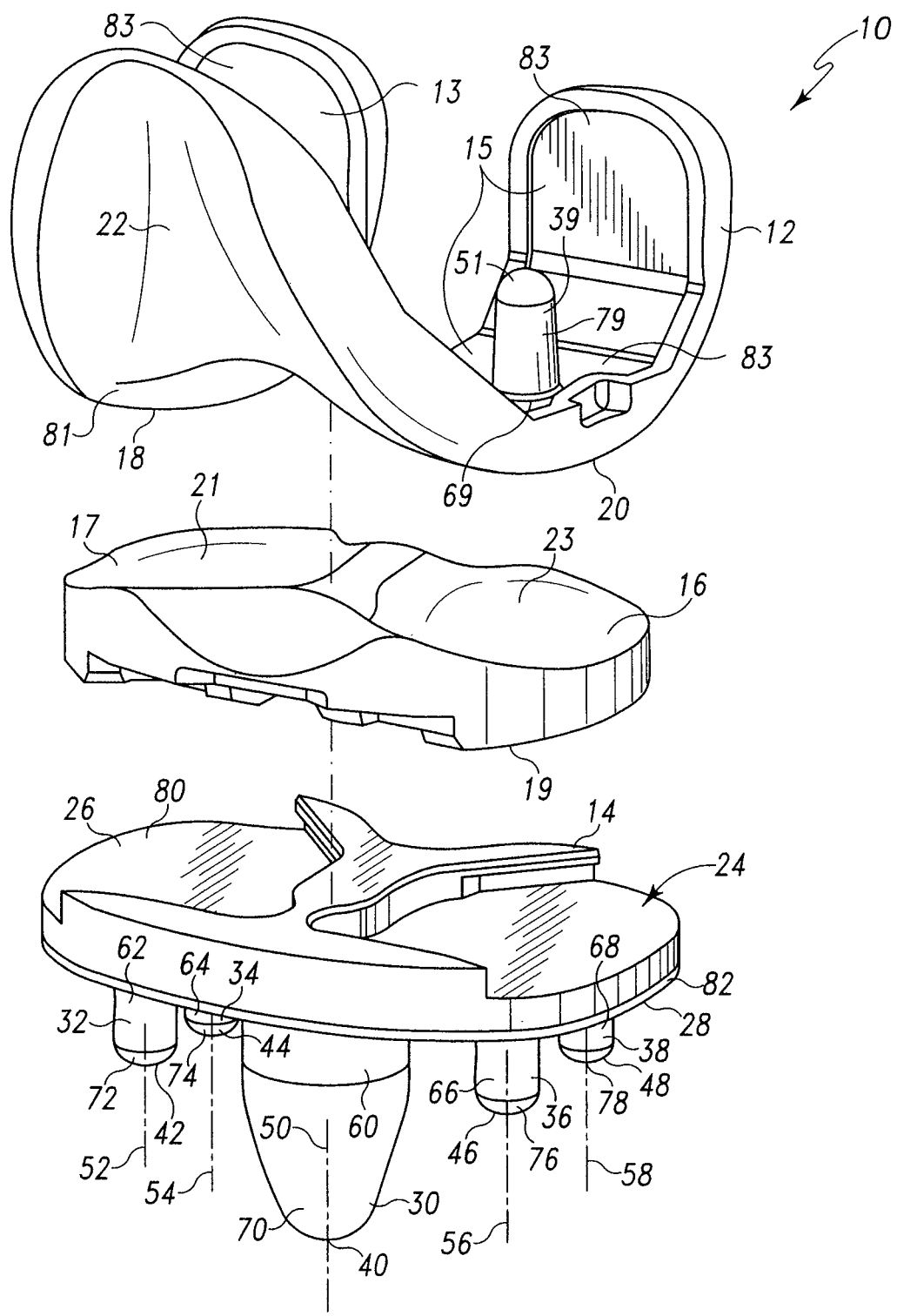
FIG. 1 is an exploded perspective view of a fixed-bearing knee prosthesis.
Figure 2:
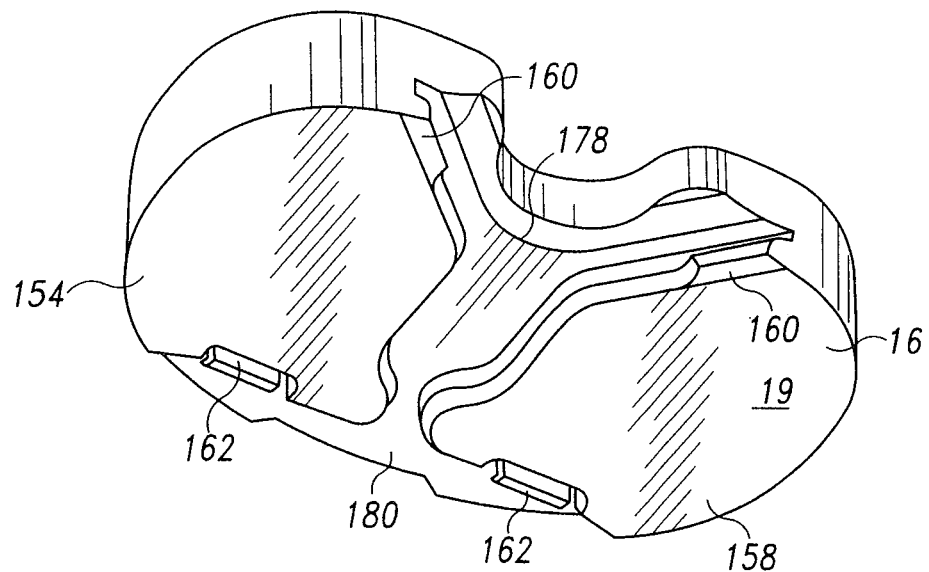
FIG. 2 is a bottom perspective view of the bearing of the knee prosthesis of FIG. 1.
Figure 3:
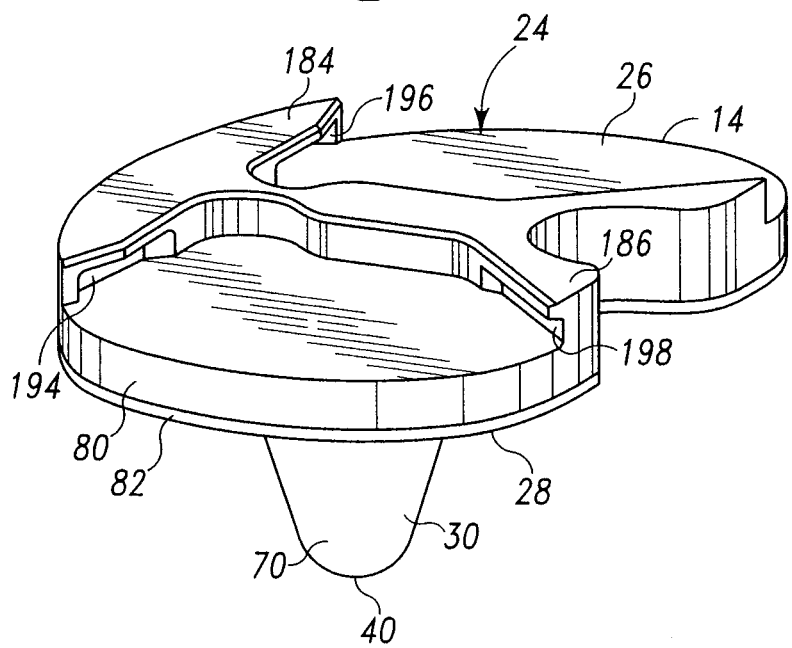
FIG. 3 is a perspective view of the tibial tray of the knee prosthesis of FIG. 1.

The following U.S. patent applications, filed concurrently herewith, are related to the present application: "Prosthesis For Cemented Fixation And Method Of Making The Prosthesis," filed by Daren L. Deffenbaugh and Anthony D. Zannis (DEP6035USCIP2, U.S. Provisional Patent Application No. 61/256,546); "Prosthesis With Cut-Off Pegs And Surgical Method," filed by Daren L. Deffenbaugh and Anthony D. Zannis (DEP6035USCIP3, U.S. Provisional Patent Application No. 61/256,574); "Prosthesis With Surfaces Having Different Textures And Method Of Making The Prosthesis," filed as a provisional patent application by Stephanie M. DeRuntz, Daren L. Deffenbaugh, Derek Hengda Liu, Andrew James Martin, Jeffrey A. Rybolt, Bryan Smith and Anthony D. Zannis (DEP6089USCIP1, U.S. Provisional Patent Application No. 61/256,468); and "Prosthesis With Composite Component," filed by Daren L. Deffenbaugh and Thomas E. Wogoman (DEP6035USCIP4, U.S. Provisional Patent Application No. 61/256,517). All of these patent applications are incorporated by reference herein in their entireties.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, there is shown a knee prosthesis 10. The knee prosthesis 10 includes a femoral component 12, a tibial tray 14, and a bearing 16. The illustrated knee prosthesis 10 is a fixed bearing knee prosthesis, meaning that no movement is intended to occur between the tibial tray 14 and the bearing 16. It should be understood that the principles of the present invention may also be applied to mobile bearing designs, such as rotating platform tibial trays, as well as to other joint prostheses.

The illustrated femoral component 12 includes two condylar articulation surfaces: a medial condyle articulation surface 18 and a lateral condyle articulation surface 20. These articulation surfaces 18, 20 are solid metal. The femoral component 12 is configured to be implanted into a surgically prepared end of the patient's femur (not shown), and is configured to emulate the configuration of the patient's natural femoral condyles. As such, the lateral condyle surface 20 and the medial condyle surface 18 are configured (e.g., curved) in a manner which mimics the condyles of the natural femur. The lateral condyle surface 20 and the medial condyle surface 18 are spaced apart from one another thereby defining an intercondylar articulation surface 22 therebetween. The intercondylar articulation surface 22 defines a patella groove shaped to receive and bear against a patella implant component (not shown). The intercondylar articulation surface 22 may comprise solid metal.

The femoral component 12 also includes bone-engaging surfaces 13, 15 opposite the articulation surfaces 18, 22. Some or all of the bone-engaging surfaces 13, 15 may comprise porous metal (as described below) conducive to bony ingrowth. Alternatively, the bone-engaging surfaces of the femoral component may include cement pockets to facilitate cementing the component to the bone.

The femoral component 12 of FIG. 1 is a cruciate retaining component, although it should be understood that the principles of the present invention are applicable to cruciate substituting prosthetic knee systems as well.

The femoral component 12 may include features of standard, commercially available implants, such as those available from DePuy Orthopaedics, Inc., Warsaw, Ind., as well as those available from other suppliers of prosthetic knee systems. The femoral component 12 may also include features described in the following U.S. patent applications, the disclosures of which are incorporated by reference herein in their entireties: "Orthopaedic Knee Prosthesis Having Controlled Condylar Curvature," Ser. No. 12/488,107 (Docket No. DEP6157USNP); "Posterior Cruciate-Retaining Orthopaedic Knee Prosthesis Having Controlled Condylar Curvature," Ser. No. 12/165,574 (Docket No. DEP6152USNP); "Orthopaedic Femoral Component Having Controlled Condylar Curvature," Ser. No. 12/165,579 (Docket No. DEP6151USNP); Ser. No. 12/165,582 (Docket No. DEP6057USNP); and "Posterior Stabilized Orthopaedic Knee Prosthesis Having Controlled Condylar Curvature," Ser. No. 12/165,575 (Docket No. DEP5923USNP).

The articulation surfaces of the femoral component 12 may be constructed from a biocompatible metal, such as stainless steel, titanium, cobalt chrome alloy or titanium alloy, although other materials may also be used. Commonly used alloys include titanium alloy Ti-6Al-4V. In one aspect of the present invention, the articulation surfaces 18, 20, 22 of the femoral component 12 comprise a titanium alloy (such as Ti-6Al-4V, for example) and the bone-engaging surfaces 13, 15 comprise titanium metal foam (such as a foam made of commercially pure titanium powder, 325 mesh (<45 um), produced by a hydride-dehydride process and that meets the ASTM F-1580 standard, available from Phelly Materials, Inc., Bergenfield, N.J., Part No. THD325 for example) or a mix of such a powder with a compatible titanium alloy powder, such as alloy Ti-6Al-4. As discussed in more detail below, the titanium metal foam may comprise a titanium foam preform bonded to the solid titanium alloy through sintering.

As shown in FIG. 1, the bearing component 16 has a proximal articulation surface 17 and a distal mounting surface 19 opposite the proximal articulation surface 17. The proximal articulation surface 17 of the bearing 16 includes a medial bearing surface 21 configured to articulate with the medial condyle 18 of the femoral component 12 and a lateral bearing surface 23 configured to articulate with the lateral condyle 20 of the femoral component 12. The bearing component 16 is modular, and is assembled with the tibial tray 14 intraoperatively and secured thereto through a mechanical interlocking mechanism, as described in more detail below.

The bearing 16 may be made of a polymeric material. Suitable polymeric materials for the bearing 16 include ultra-high molecular weight polyethylene (UHMWPE). The UHMWPE may comprise a cross-linked material, for example. Techniques for crosslinking, quenching, or otherwise preparing UHMWPE are described in numerous issued U.S. patents, examples of which include: U.S. Pat. No. 5,728,748 (and its counterparts) issued to Sun, et al.; U.S. Pat. No. 5,879,400 issued to Merrill et al.; U.S. Pat. No. 6,017,975 issued to Saum, et al.; U.S. Pat. No. 6,242,507 issued to Saum et al.; U.S. Pat. No. 6,316,158 issued to Saum et al.; U.S. Pat. No. 6,228,900 issued to Shen et al.; U.S. Pat. No. 6,245,276 issued to McNulty et al.; and U.S. Pat. No. 6,281,264 issued to Salovey et al. The disclosure of each of these U.S. patents is incorporated by reference herein in their entireties. The UHMWPE of the bearing material may be treated to stabilize any free radicals present therein, such as through the addition of an antioxidant such as vitamin E. Techniques for stabilizing UHMWPE with antioxidants are disclosed, for example, in U.S. Pat. Pub. No. 20070293647A1 (Ser. No. 11/805,867) and U.S. Pat. Pub. No. 20030212161A1 (Ser. No. 10/258,762), both entitled "Oxidation-Resistant And Wear-Resistant Polyethylenes For Human Joint Replacements And Methods For Making Them," the disclosures of which are incorporated herein in their entireties. It should be understood that the present invention is not limited to any particular UHMWPE material or to UHMWPE material for the bearing 16 unless expressly called for in the claims. It is expected that other materials for the bearing 16 are or will become available that will be useful in applying the principles of the present invention.

The tibial tray 14 includes a platform 24 having a solid metal proximal mounting surface 26 and an opposite distal bone-engaging surface 28. The illustrated tibial tray 14 also includes a plurality of extensions 30, 32, 34, 36, 38 extending distally from the distal bone-engaging surface 28 of the platform to distal ends 40, 42, 44, 46, 48 along longitudinal axes 50, 52, 54, 56, 58 intersecting the distal surface 28 of the platform 24. Each extension 30, 32, 34, 36, 38 has an axial length, shown, for example, as $L_1$ and $L_2$ in FIG. 5 and a thickness, shown, for example, as $T_1$ and $T_2$ in FIG. 5.

The femoral component 12 may also include extensions. For example, pegs may extend proximally from the bone-engaging surfaces 13, 15 of the femoral component 12. One such peg is illustrated in FIG. 1 at 39. This peg also has a thickness and a length.

In the illustrated femoral component and tibial tray, each extension 30, 32, 34, 36, 38, 39 extends outward from a junction with the bone-engaging surfaces 13, 15, 28 of their respective implant components 12, 14 to their opposite ends 40, 42, 44, 46, 48, 51. Examples of such junctions are shown in FIG. 1 at 69, in FIG. 5 at 60, 62 and 66 and in FIG. 7 at 60A, 62A, 66A. The extensions 30, 32, 34, 36, 38, 39 have exposed outer surfaces past the junctions; examples of such exposed outer surfaces are shown at 79 in FIG. 1, at 70, 72 and 76 in FIG. 5 and at 70A, 72A and 76A in FIG. 7.

The extensions 30, 32, 34, 36, 38 of the first and second illustrated tibial tray embodiments define a stem 30, 30A and four spaced pegs 32, 34, 36, 38, 32A, 34A, 36A, 38A. The stem 30, 30A and pegs 32, 34, 36, 38, 32A, 34A, 36A, 38A are configured to be implanted into a surgically prepared end of a patient's tibia (not shown) and are configured for stabilizing the tibial component 14, 14A when implanted in a bone of a patient. The stem 30, 30A is generally in the central sagittal plane of the tibial component, and the pegs 32, 34, 36, 38, 32A, 34A, 36A, 38A are spaced from the central sagittal plane of the tibial component.

Figure 4:
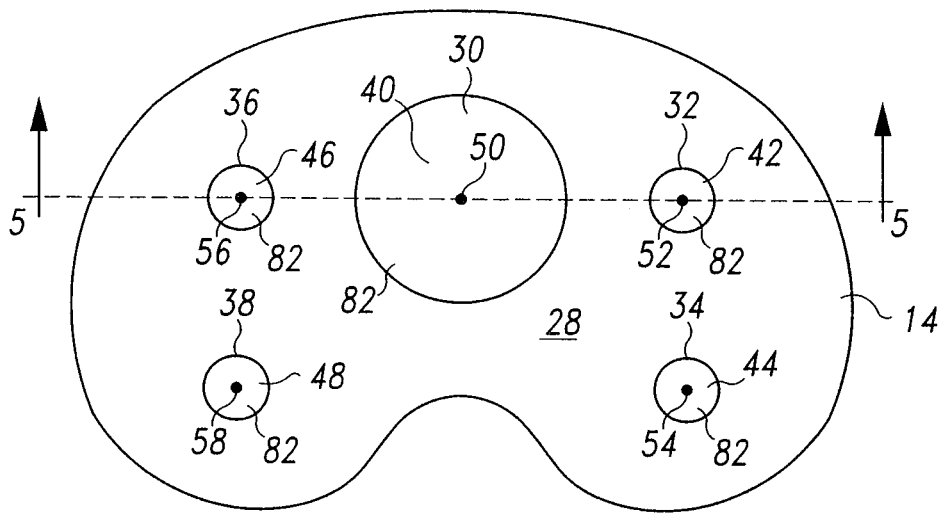
FIG. 4 is a bottom plan view of the tibial tray of FIG. 1.
Figure 5:
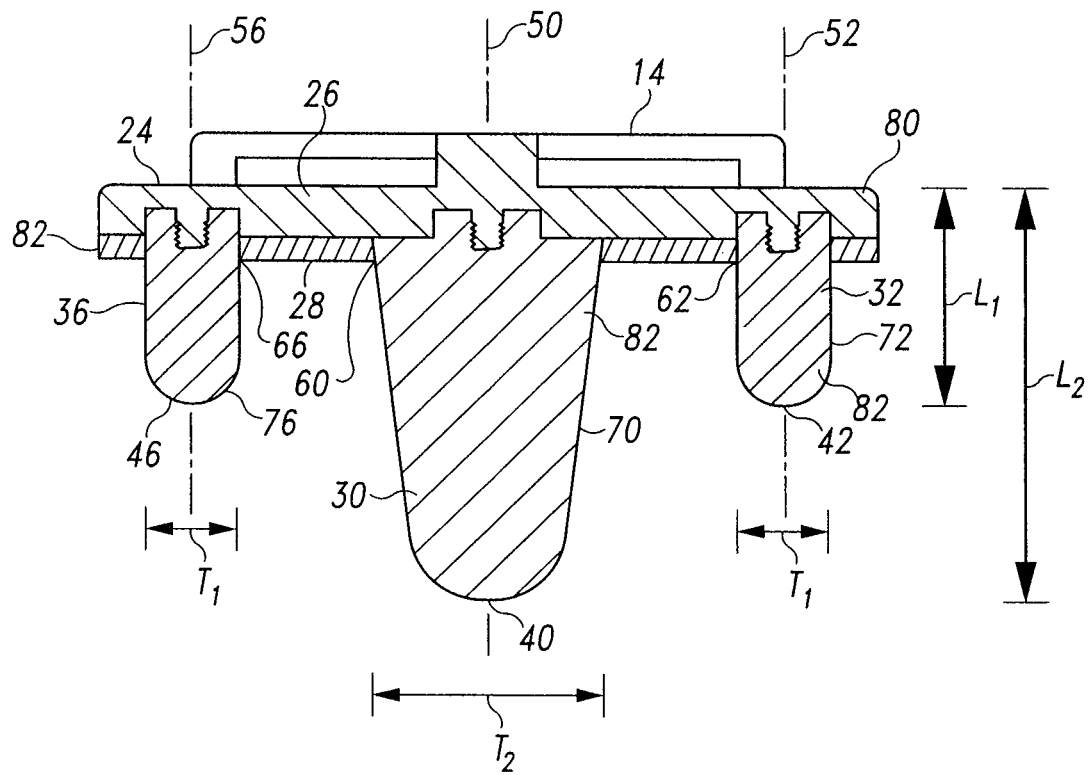
FIG. 5 is a cross sectional view of the tibial tray of FIG. 4 taken along the line 5-5 of FIG. 4, as viewed in the direction of the arrows.
Figures 12, 13:
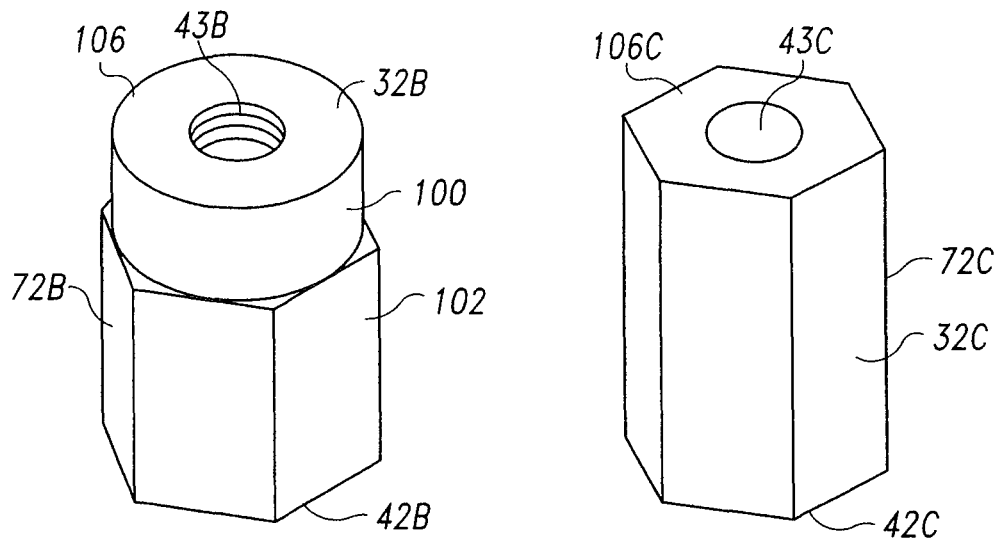
FIG. 12 is a perspective view of an alternative form of peg that may be used for the tibial tray or femoral component.
FIG. 13 is a perspective view of another alternative form of peg that may be used for the tibial tray or femoral component.

The stem 30, 30A may be shaped as a standard stem for tibial trays, tapering from the junction 60, 60A with the bone-engaging surface 28, 28A of the tray 14, 14A to its distal end 40, 40A. Each of the tibial pegs 32, 34, 36, 38 in the embodiment of FIGS. 1, 4 and 5 is circular in transverse cross-section and end view. Other shapes may also be used for the pegs. The pegs may be tapered or cylindrical. The pegs may be a combination of shapes, such as a combination of cylindrical and hexagonal, as shown in FIG. 12 at 32B. Alternatively, the pegs may be hexagonal in cross-section and end view, as shown in FIG. 13 at 32 C. In FIGS. 12 and 13, the reference numbers are the same as those used in the description of the embodiment of FIGS. 1, 4 and 5 for similar parts, followed by the letters "B" and "C".

The distal end surfaces of the stem and pegs could be flat, spheroidal or some other shape. In the embodiment of FIGS. 1, 4 and 5, the free ends 40, 42, 44, 46, 48, 51 are generally spheroidal. In the embodiments of FIGS. 12 and 13, the distal ends 42B, 42C are flat. It should be understood that the invention is not limited to any particular shape of peg or stem unless expressly set forth in the claims.

Figure 6:
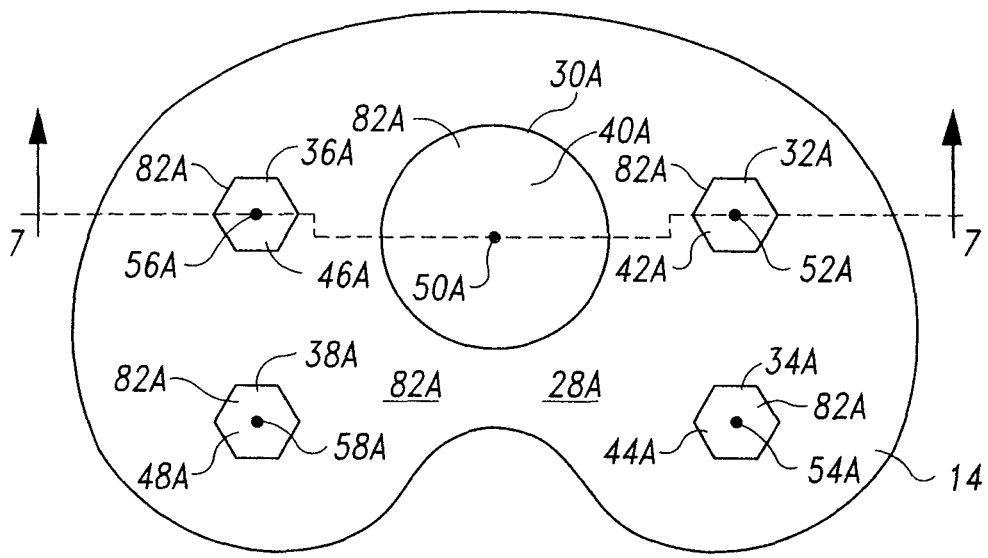
FIG. 6 is a bottom plan view of an alternative embodiment of a tibial tray that may be used in the present invention.
Figure 7:
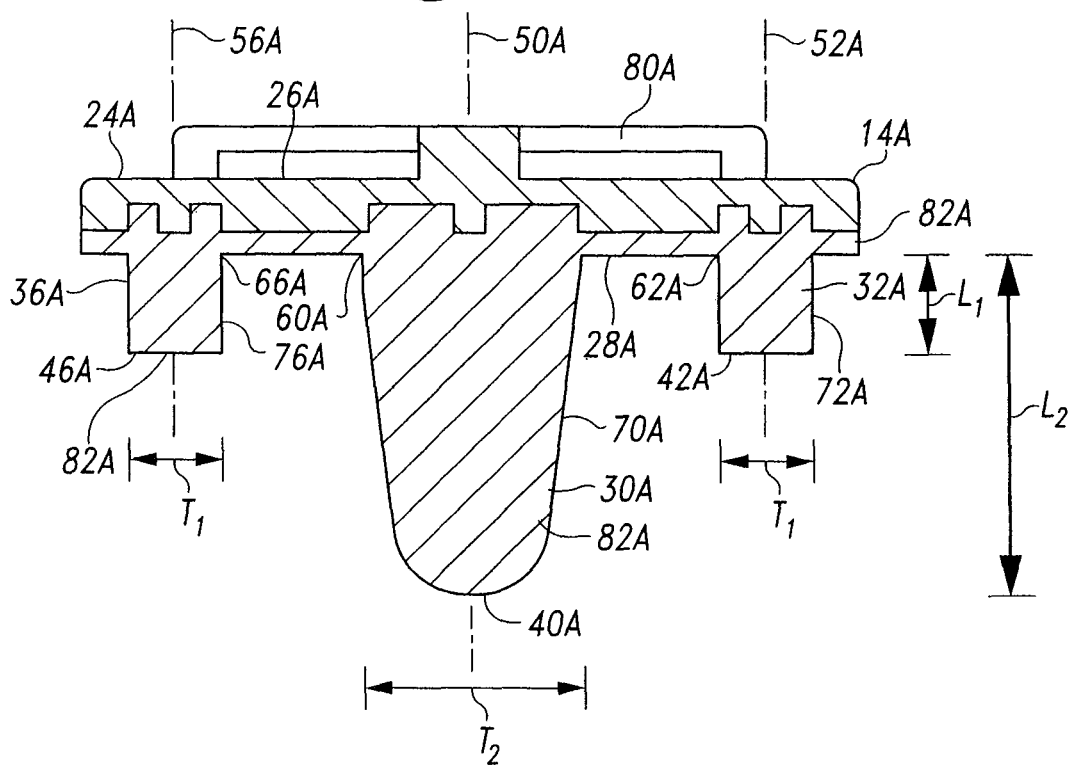
FIG. 7 is a cross sectional view of the tibial tray of FIG. 6 taken along the line 7-7 of FIG. 6, as viewed in the direction of the arrows.

Another alternative embodiment is illustrated in FIGS. 6-7, where the same reference numbers have been used as those used in describing corresponding or similar parts in the embodiment of FIGS. 1 and 4-5, followed by the letter "A". As described in more detail below, in the embodiment of FIGS. 6-7, all of the extensions 30A, 32A, 34A, 36A, 38A are part of a single integral preform. The embodiments may share features as described above and below. Differences between the embodiments are described above and below.

The tibial trays 14, 14A illustrated in FIGS. 1 and 3-7 are composites of two materials; each tray 14, 14A includes solid metal portions 80, 80A and porous metal portions 82, 82A. The solid metal portions 80, 80A of the illustrated tibial trays 14, 14A define the proximal mounting surfaces 26, 26A of the platforms 24, 24A and bear against the distal mounting surface 19 of the bearing component 16 when assembled. The femoral component of FIG. 1 may also be a composite of a solid metal portion 81 and a porous metal portion 83, with the solid metal portion 81 defining the articulating surfaces 18, 20, 22.

The porous metal portions 82, 82A, 83 of the tibial tray 14, 14A and femoral component 12 define the distal bone-engaging surfaces 28, 28A of the tibial platform 24, 24A and the bone-engaging surfaces 13, 15 of the femoral component 12. These porous metal surfaces 13, 15, 28, 28A face the bone of the resected proximal surface of the tibial plateau and resected surfaces of the distal femur when implanted, and define a material that is conducive to bone ingrowth to allow for uncemented fixation of the tibial platform 24, 24A to the proximal tibia and the femoral component 12 to the distal femur. As described in more detail below, the porous metal portion 82, 82A of the tray 14, 14A extends proximally from the distal bone-engaging surface 28, 28A and is sintered to the solid metal portion 80, 80A at a location between the distal bone-engaging surface 28, 28A and the proximal mounting surface 26, 26A of the platform 24, 24A. The femoral component 12 is similarly constructed, with the porous metal portion 83 sintered to the solid metal portion 81 at a location between the bone-engaging surfaces 13, 15 and the articulating surfaces 18, 20, 22.

Figure 8:
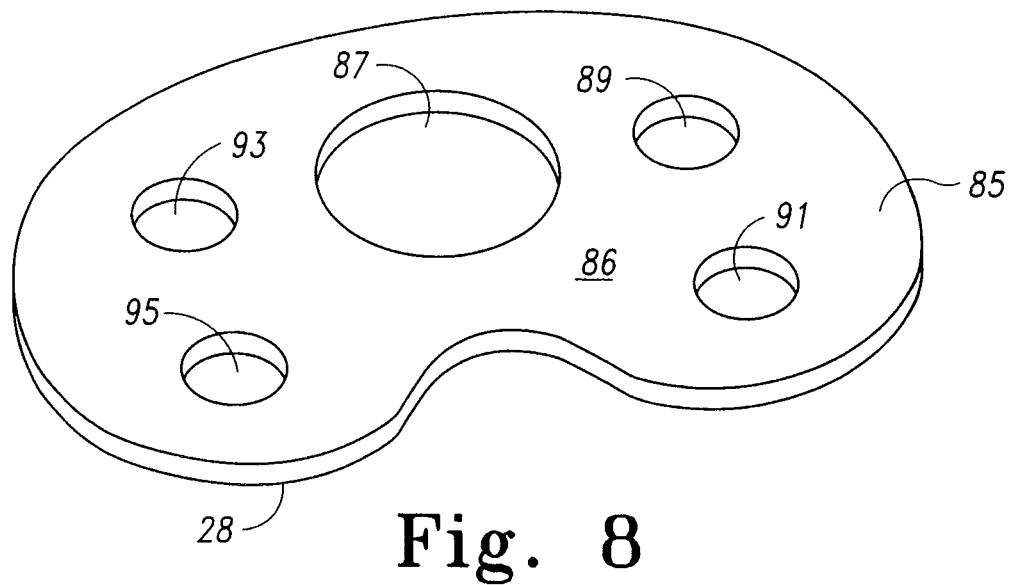
FIG. 8 is a perspective view of a preform for the tibial tray platform portion of the porous metal portion of the tibial tray of FIGS. 1-5.
Figure 9:
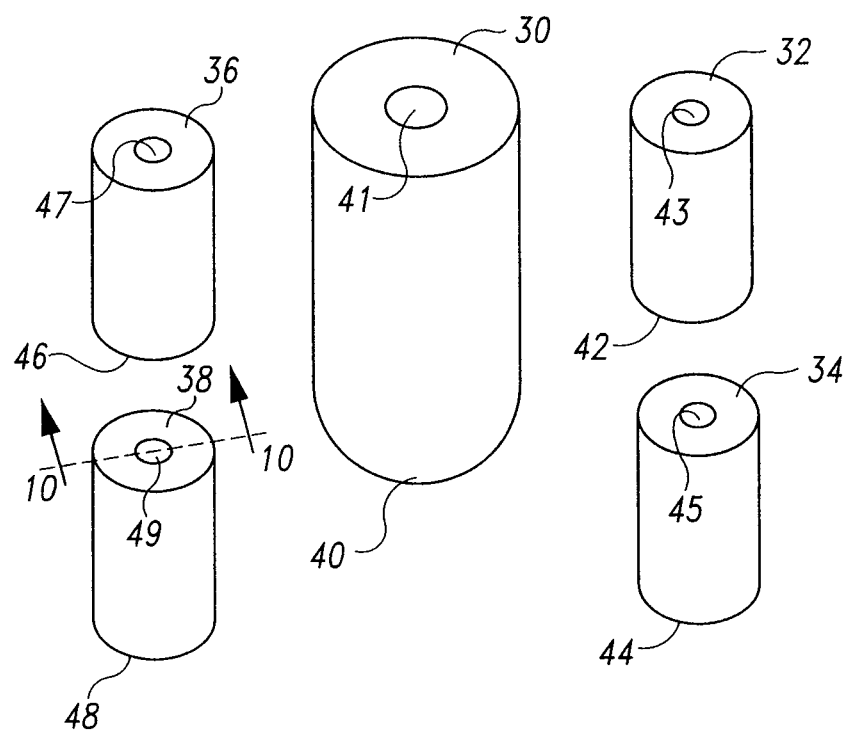
FIG. 9 is a perspective view of a set of preforms for the extensions of the porous metal portion of the tibial tray of FIGS. 1-5.

The porous metal portions 82, 82A, 83 of the tibial tray 14 and femoral component 12 may comprise preforms or plurality of preforms. A first example of a set of porous metal preforms for a tibial tray 14 is illustrated in FIGS. 8-9. This set of porous metal preforms includes a base preform 85 with an upper surface 86 opposite from the distal bone-engaging surface 28. The upper surface 86 becomes the interface with the solid metal portion 80 of the tray 14 when the porous metal base preform 85 is sintered to the solid metal portion 80 to make the tibial tray 14. As described in more detail below, the first illustrated base preform 85 includes a plurality of smooth cylindrical bores or openings 87, 89, 91, 93, 95 extending from the upper surface 86 to the distal bone-engaging surface 28.

Figure 10:
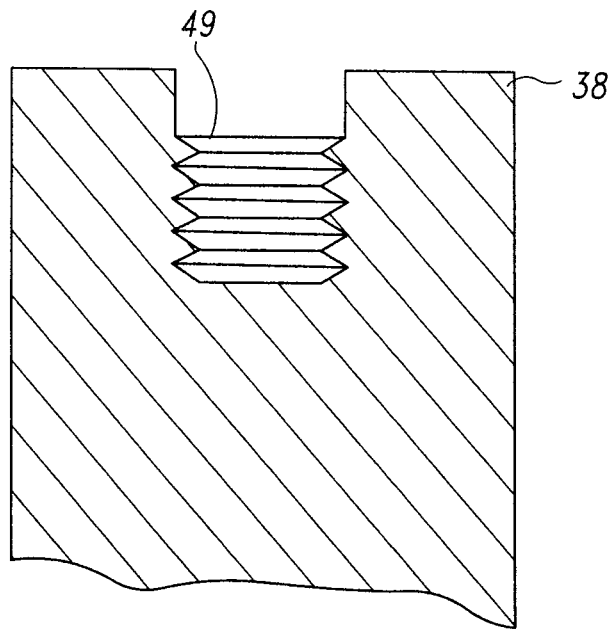
FIG. 10 is a cross sectional view of the proximal end of the peg preform of FIG. 9 taken along line 10-10 of FIG. 9, as viewed in the direction of the arrows.

As illustrated in FIG. 9, the extensions 30, 32, 34, 36, 38 in the first set of porous metal preforms are discrete components, separate from the base preform 85 before being sintered together. The extension preforms are circular in transverse cross-section, with diameters substantially the same as the diameters of the bores 87, 89, 91, 93, 95 in the base preform 85. Portions of the extensions adjacent to the proximal ends of the extensions fit through the bores 87, 89, 91, 93, 95 and make contact with the walls of the base preform so that the preform 85 and extensions 87, 89, 91, 93, 95 may be sintered together. The proximal ends of the discrete extensions include blind bores 41, 43, 45, 47, 49 aligned along the longitudinal axes 50, 52, 54, 56, 58 of the extensions 30, 32, 34, 36, 38. The bores 41, 43, 45, 47, 49 are threaded in this embodiment. For clarity of illustration, FIG. 9 does not show the threads in these bores 41, 43, 45, 47, 49. An example of such a threaded bore 49 is shown in longitudinal cross-section in FIG. 10.

Other shapes of extensions may be used in combination with the base preform 85. For example, the extensions corresponding to the pegs may comprise a combination of a cylindrical portion and a portion that is hexagonal in transverse cross-section. Such a peg is shown in FIG. 12 at 32B; the cylindrical portion is shown at 100 and the hexagonal portion is shown at 102. This peg preform also has a flat end surface 42B opposite the end surface 106 that includes the threaded bore 43B.

Another example of an extension that may be used in the present invention is shown in FIG. 13 at 32C. In this example, the extension 32C is hexagonal in transverse cross-section and in end view. The extension includes two flat ends 42C, 106C with a blind bore 43C in one end 106C. In this example, the blind bore 43C is not threaded. Instead, the walls of the bore 43C define a Morse taper bore for receipt of a Morse taper post as described in more detail below. The walls defining the bore 43C may be tapered at an angle of, for example 3-5°. The bore is widest at the end 106C and most narrow between the end 106C and the end 42C. Peg preforms such as those illustrated in FIG. 13 could be used with a tibial platform preform similar to that illustrated in FIG. 8, except the bores or holes 89, 91, 93, 95 would have hexagonal shapes to receive and hold the extension 32C.

Figure 14:
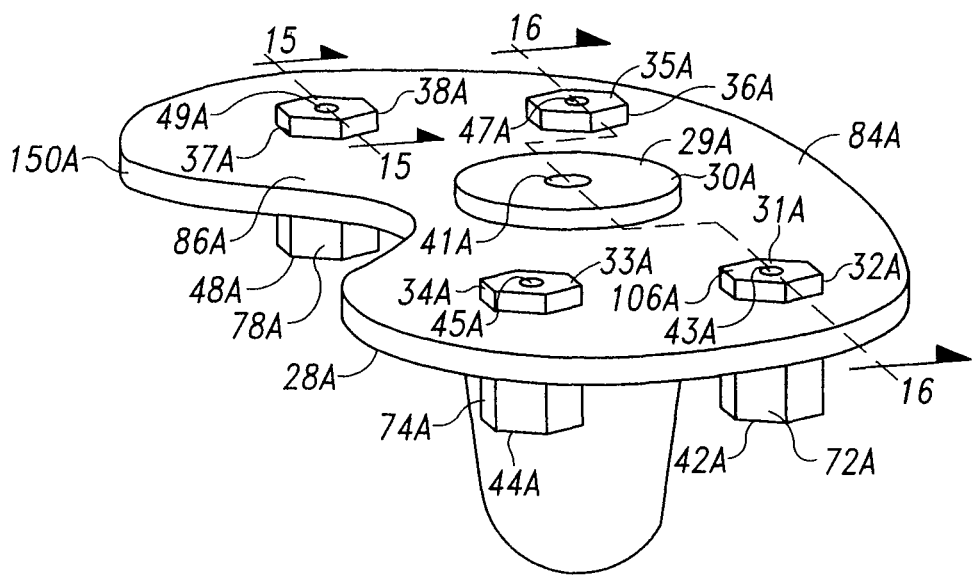
FIG. 14 is a perspective view of an alternative form of preform that may be used for the porous metal portion of the tibial tray.
Figure 15:
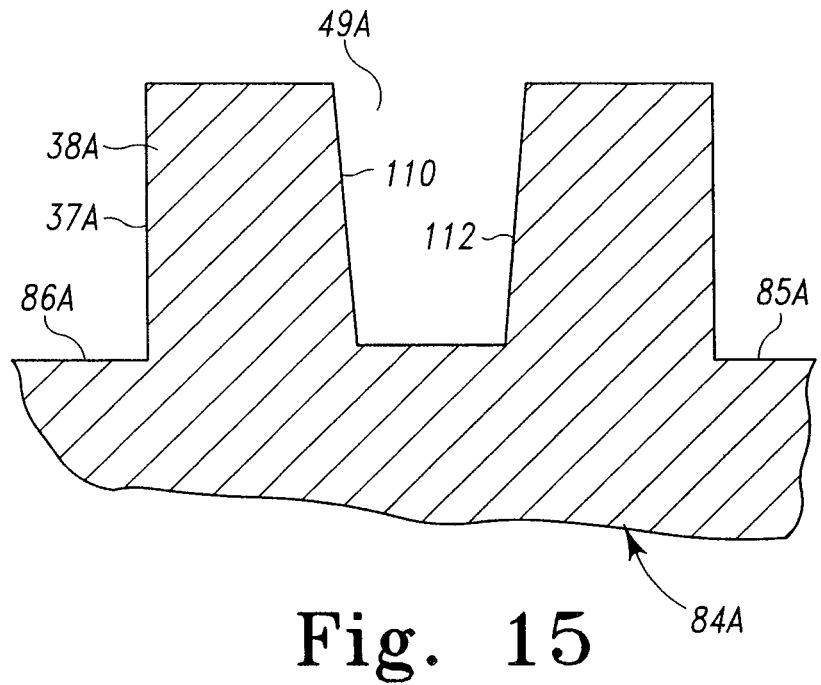
FIG. 15 is a cross sectional view of the proximal end of a portion of the preform of FIG. 14, taken along line 15-15 of FIG. 14, as viewed in the direction of the arrows.

An example of a porous metal preform utilizing extensions shaped like those of FIG. 13 is shown in FIG. 14. In this example, the porous metal preform 84A includes a base portion 85A and integral extensions 30A, 32A, 34A, 36A, 38A. The extensions 32A, 34A, 36A, 38A correspond with pegs and the extension 30A corresponds with the stem of the tibial tray. In this embodiment, the extension 30A corresponding with the stem is circular in transverse cross-section, although it should be understood that other shapes may be used. On the proximal side of the base 85A, an annular raised portion 29A, 31A, 33A, 35A, 37A of each extension extends above the planar proximal surface 86A of the base 85A. Each extension includes a longitudinal bore or opening 41A, 43A, 45A, 47A, 49A. As discussed above with respect to FIG. 13, in this embodiment, the longitudinal bores or openings 41A, 43A, 45A, 47A, 49A are Morse taper bores tapering in a distal direction. An enlarged cross-sectional view of one of the annular raised portions 37A and its associated bore 49A is shown in FIG. 15 as an illustrative example; the walls 110, 112 defining the tapered bore 49A may be angled at any suitable angle for a Morse taper bore, such as, for example, 3-5°. The annular projections 29A, 31A, 33A, 35A, 37A may be cylindrical in shape, like that shown at 29A, or may have some other shape, such as the hexagonal shape (in transverse cross-section and plan view) like those shown at 31A, 33A, 35A and 37A.

Figure 16:
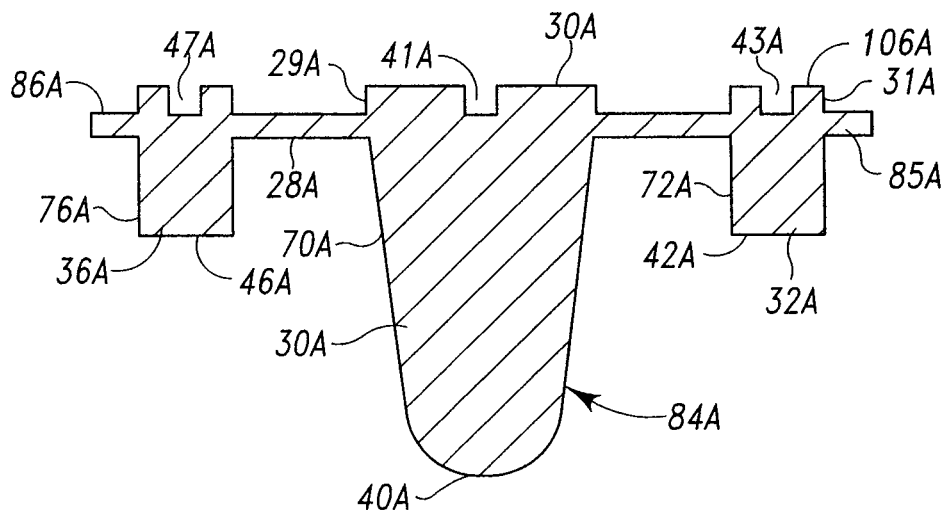
FIG. 16 is a cross sectional view of the porous metal preform of FIG. 14, taken along line 16-16 of FIG. 14, as viewed in the direction of the arrows.

A cross-section of the porous metal preform 84A is shown in FIG. 16 as an example. The porous metal preform 84A can be made as a single, integral piece in the molding process and can be otherwise processed in standard ways, such as by machining to create particular features. FIG. 7 illustrates the preform 84A of FIGS. 14-16 in combination with a solid metal portion 80A to form the tibial tray 14A.

Figure 17:
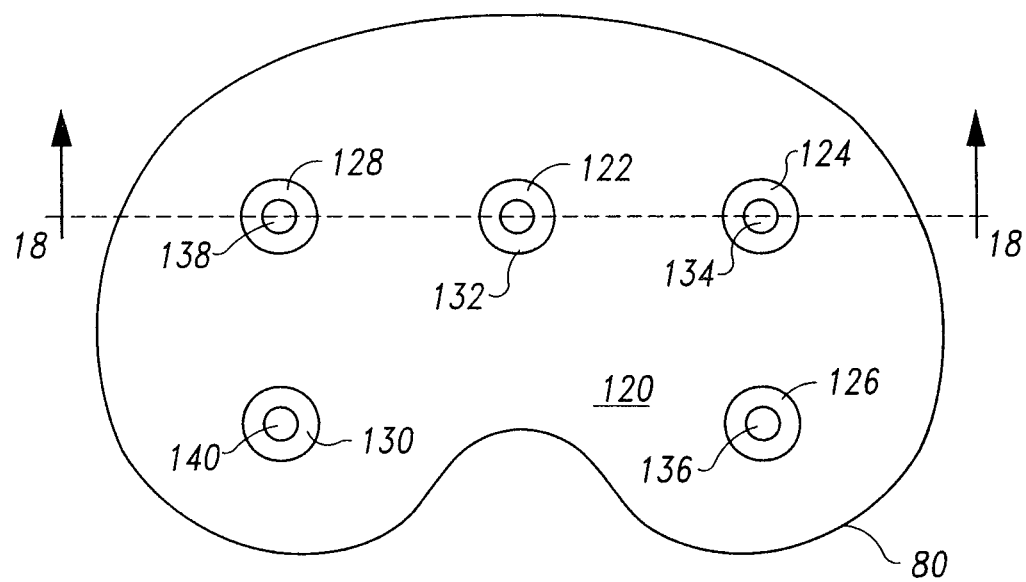
FIG. 17 is a bottom plan view of the solid metal preform for the tibial tray of FIGS. 4-5, for use with the porous metal preforms of FIGS. 8-9.
Figure 19:
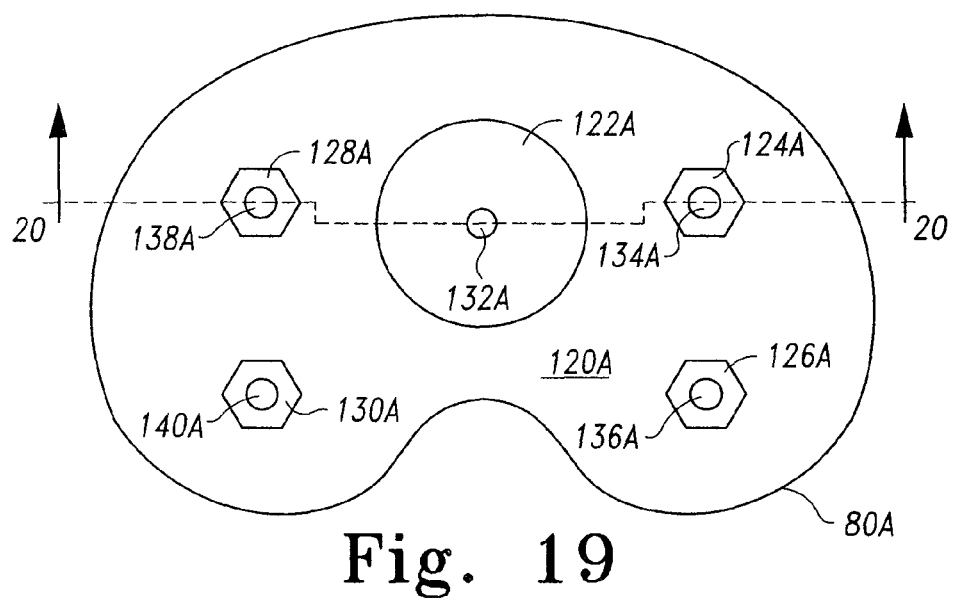
FIG. 19 is a bottom plan view of an alternative solid metal preform, for use with the porous metal preform of FIGS. 14 and 16.

Referring back to the solid metal portion 80 of the tibial tray 14, a first example of a distal surface 120 of the solid metal portion is illustrated in FIG. 17. The distal surface 120 is opposite the proximal mounting surface 26 of the platform 24 of the tibial tray 14 of FIG. 1. As there shown, the distal surface 120 includes a plurality of recesses 122, 124, 126, 128, 130. A stud 132, 134, 136, 138, 140 is present within each recess 122, 124, 126, 128, 130. The distal surface of a second example of the solid metal portion 80A of a tibial tray is illustrated in FIG. 19. As there shown, the distal surface 120A also includes a plurality of recesses 122A, 124A, 126A, 128A, 130A. A stud 132A, 134A, 136A, 138A, 140A is present within each recess 122A, 124A, 126A, 128A, 130A.

Figure 18:
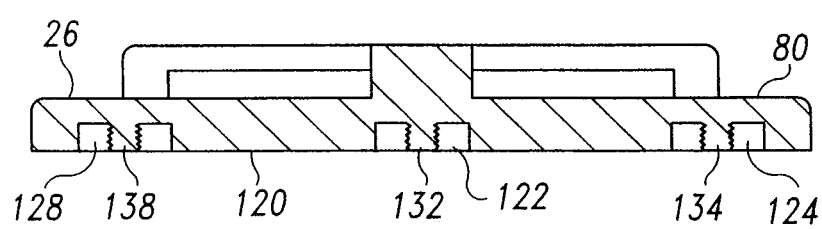
FIG. 18 is a cross sectional view of the solid metal preform of FIG. 17, taken along line 18-18 of FIG. 17, as viewed in the direction of the arrows.

The recesses 122, 124, 126, 128, 130 in the embodiment of FIGS. 17-18 are configured to receive the cylindrical ends of the extensions 30, 32, 34, 36, 38 and the studs 132, 134, 136, 138, 140 are threaded and complementary to the threaded bores 41, 43, 45, 47, 49 so that the extensions 30, 32, 34, 36, 38 may be threaded onto the studs 132, 134, 136, 138, 140 to mount the extensions to the studs 132, 134, 136, 138, 140. Preferably, the recesses 122, 124, 126, 128, 130 and extensions 30, 32, 34, 36, 38 are shaped so that there is metal-to-metal contact between the outer surfaces of the extensions 30, 32, 34, 36, 38 and the walls defining the recesses 122, 124, 126, 128, 130 so that the extensions 30, 32, 34, 36, 38 may be sintered to the solid metal portion 80.

Figure 20:
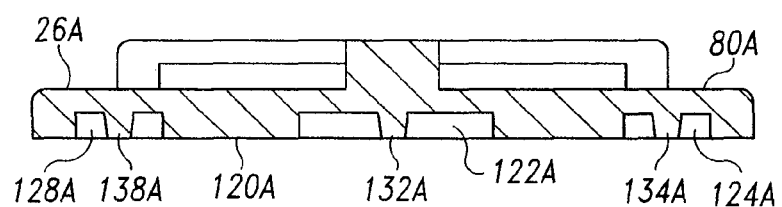
FIG. 20 is a cross sectional view of the solid metal preform of FIG. 19, taken along line 20-20 of FIG. 19, as viewed in the direction of the arrows.

The recesses 122A, 124A, 126A, 128A, 130A in the embodiment of FIGS. 19-20 are configured to receive the annular raised portions 29A, 31A, 33A, 35A, 37A of the preform 84A (or ends of the extensions 30A, 32A, 34A, 36A, 38A) and the studs 132A, 134A, 136A, 138A, 140A are tapered and complementary to tapered bores 41A, 43A, 45A, 47A, 49A so that the preform 84A may be frictionally mounted onto the studs 132A, 134A, 136A, 138A, 140A. The recesses 122A, 124A, 126A, 128A, 130A and annular raised portions 29A, 31A, 33A, 35A, 37A have complementary shapes (hexagonal in transverse cross-sections) so that there is metal-to-metal contact between the annular raised portions 29A, 31A, 33A, 35A, 37A and the walls defining the recesses 122A, 124A, 126A, 128A, 130A so that the preform 84A may be sintered to the solid metal portion 80A.

Figure 11:
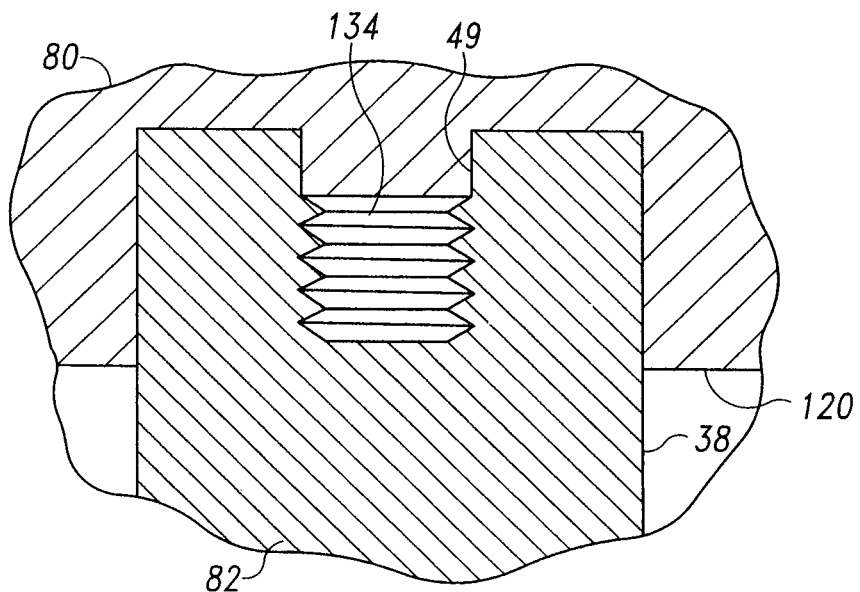
FIG. 11 is a cross sectional view similar to FIG. 10, showing the proximal end of the peg preform mounted on the solid metal portion of the tray.
Figure 21:
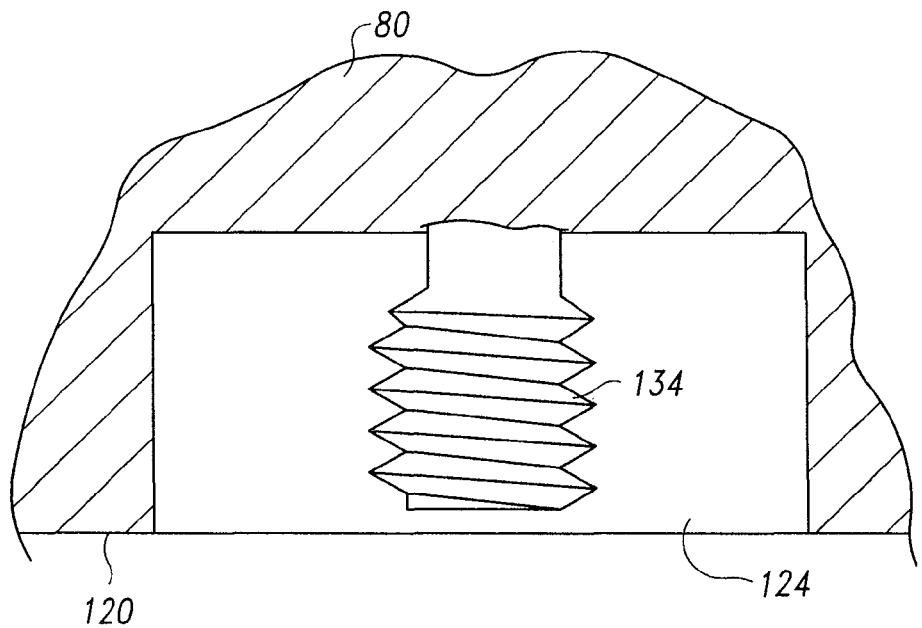
FIG. 21 is an enlarged partial cross sectional view of a portion of the solid metal preform of FIGS. 17-18
Figure 22:
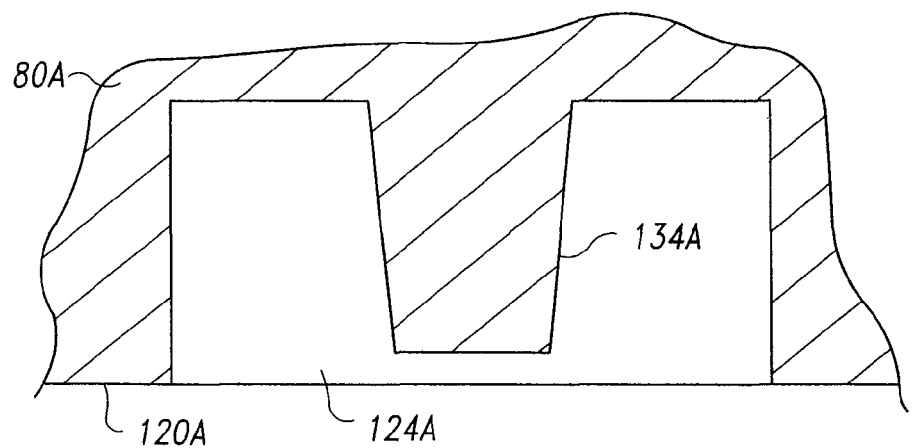
FIG. 22 is an enlarged cross sectional view of a portion of the solid metal preform of FIGS. 19-20.

Examples of configurations for studs are shown in FIGS. 21-22. The studs may be threaded, such as stud 134 shown in FIG. 21 to allow for a threaded connection between the studs and the corresponding threaded bores of the extensions; such a connection is illustrated in FIG. 11, where threaded stud 134 is shown connected with extension 38 through such a threaded connection.

Figure 23:
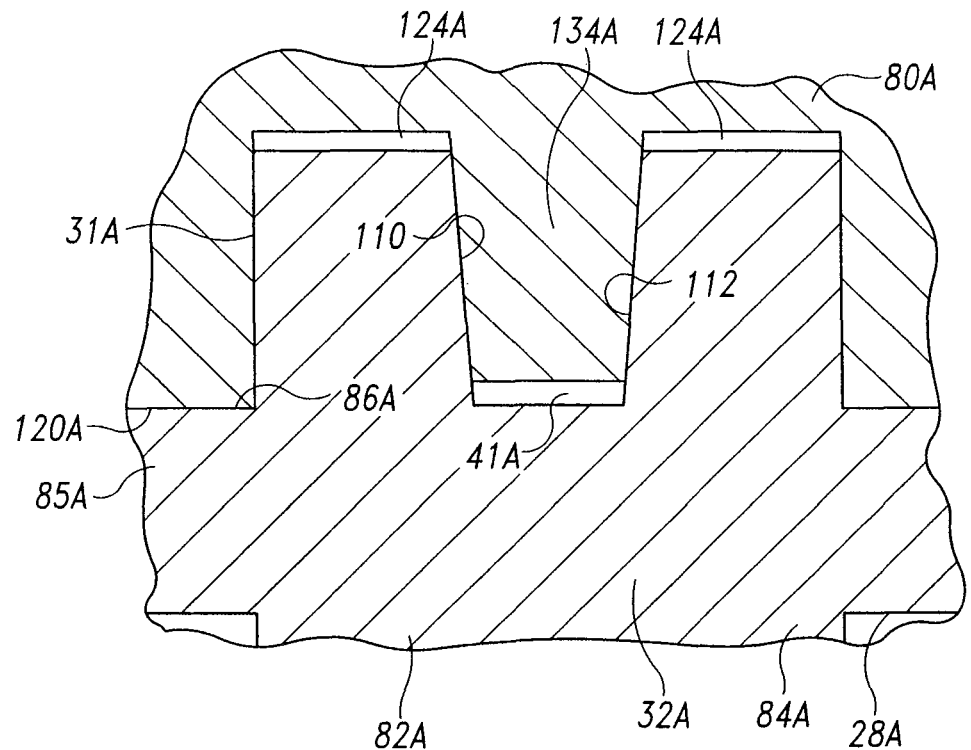
FIG. 23 is a view similar to FIG. 22, showing in cross section a portion of the solid metal preform of FIGS. 19-20 and 22 assembled with the porous metal preform of FIGS. 14 and 16.

The studs may alternatively comprise Morse taper posts having a Morse taper (generally about 3-5°); such a stud is shown in FIG. 22 at 134A. Generally, the studs are sized, shaped and positioned to be received within the Morse taper bore (generally about 3-5°) of a corresponding extension so that the extensions may be mounted on the studs. Such a connection is illustrated in FIG. 23, where Morse taper stud 134A is shown engaged with Morse taper bore 41A in preform 84A. It should be understood that the mounting mechanisms illustrated in FIGS. 21-22 are provided as examples only; other suitable structures may be used for mounting the extensions 30, 32, 34, 36, 38 and preform 84A to the corresponding solid metal portion 80, 80A, and the invention is not limited to any particular mounting structure unless expressly called for in the claims.

Figure 28:
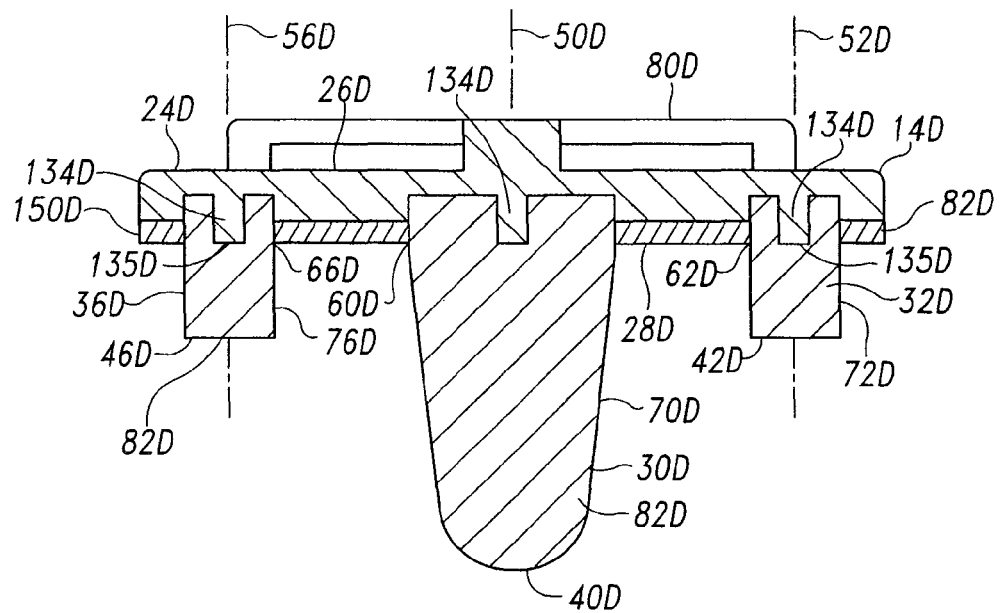
FIG. 28 is a cross-sectional view, similar to FIGS. 5 and 7, of an alternative embodiment of a tibial tray that may be used in the present invention.
Figure 29:
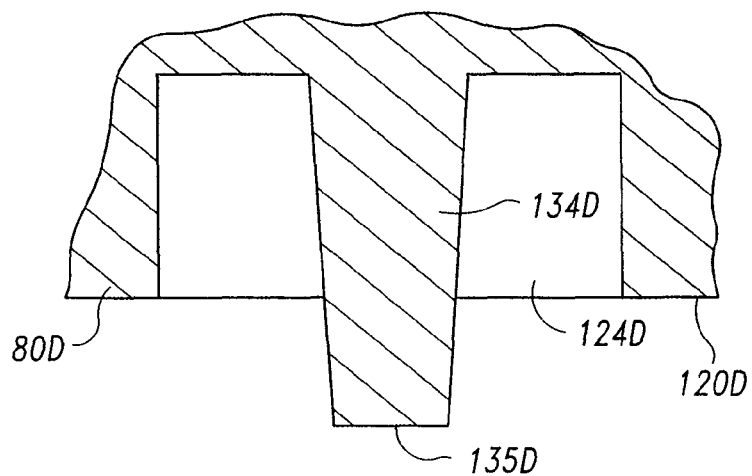
FIG. 29 is an enlarged cross-sectional view of one of the studs and recesses of the metal preform of FIG. 28.
Figure 30:
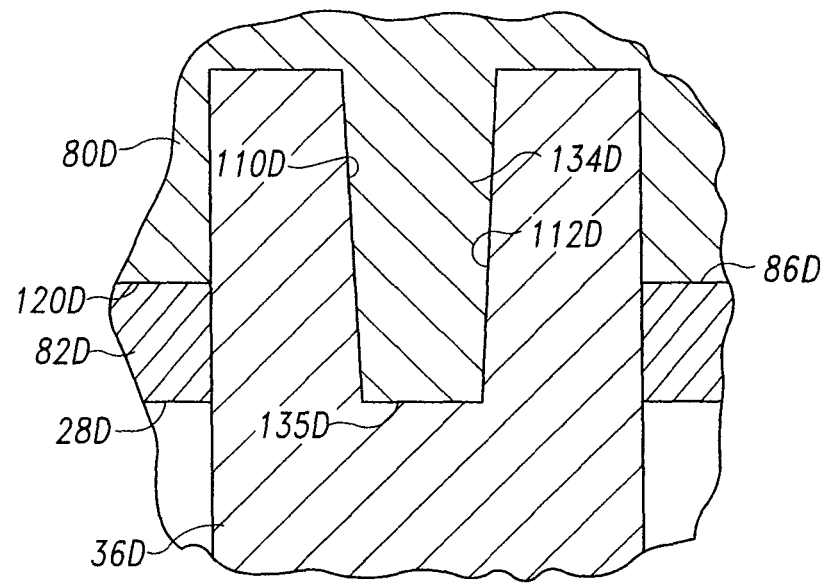
FIG. 30 is a cross-sectional view similar to FIG. 29, showing the proximal end of the peg preform mounted on the stud of FIG. 29.

In the embodiments of FIGS. 5, 7, 11, 18 and 20-23 the studs 134, 134 have free ends 135, 135A that do not extend beyond the plane of the distal surface 120, 120A of the solid metal portion 80, 80A of the tibial tray 14, 14A. An alternative embodiment of a tibial tray with longer studs is illustrated in FIGS. 28-30, where the same reference numbers have been used as those used in describing corresponding or similar parts in the embodiments of FIGS. 1 4-7, 11, 18 and 20-23 followed by the letter "D". In the embodiment of FIGS. 28-30, the free ends 135D of the studs extend beyond the plane of the distal surface 120D of the solid metal portion 80D of the tibial tray 14D. When assembled with the porous metal preform 82D as shown in FIGS. 28 and 30, the ends 135D of the studs extend to the plane of the bone-engaging surface 28D of the porous metal portion of the tibial tray 14D.

In addition, it should be understood that the complementary mounting structures may be reversed, with the studs being present on the extensions and the complementary recesses being provided on the solid metal portion of the tibial tray.

The configuration of the proximal mounting surface 26, 26A of the solid metal portion 80, 80A of the tibial tray 14, 14A may vary depending on the type of implant. For example, if the prosthesis is a rotating platform type of mobile bearing knee prosthesis, the proximal mounting surface 26, 26A of the tibial tray 14, 14A and the distal mounting surface 19 of the bearing 16 will be smooth to allow for rotation of the bearing on the mounting surface 26, 26A of the tibial tray 14, 14A. The embodiment illustrated in FIG. 1 is a fixed bearing design; the proximal mounting surface 26 of the tibial tray 14 and the distal mounting surface 19 of the bearing 16 in this illustration include complementary locking features that eliminate or at least minimize any relative movement between the bearing 16 and the tibial tray 14 when these components are assembled. These complementary locking features in the illustrated embodiment include pedestals 154, 158, tabs 160, 162 and recesses 178, 180 on the distal surface 19 of the bearing 16 and buttresses 184, 186 and undercuts 194, 196, 198 on the proximal mounting surface 26 of the solid metal portion 80 of the tibial tray 14. Detailed descriptions of this and other designs for fixed bearing tibial trays may be found, for example, in the following U.S. patent and patent application, the disclosures of which are incorporated by reference herein in their entireties: U.S. Pat. No. 7,628,818, entitled "Fixed-Bearing Knee Prosthesis Having Interchangeable Components", filed on Sep. 28, 2007; U.S. patent application Ser. No. 11/860,833, entitled "Fixed-Bearing Knee Prosthesis", filed on Sep. 25, 2007 and published as US 20090082873 A1.

Preferably, the solid metal portion 80, 80A of the tibial tray 14, 14A is a solid metal preform, made from a standard titanium metal alloy. A suitable alloy for this purpose is Ti-6Al-4V. This alloy is advantageous in that it may be sintered to a porous metal portion made from commercially pure titanium powder. This same material may be used for the solid metal portion of the femoral component 12 as well. It should be understood that some of the advantages of the present invention may be achieved with other materials, such as a standard cobalt chrome molybdenum alloy; the present invention is not limited to any particular metal or alloy for the solid metal portions unless expressly called for in the claims.

Preferably, the porous metal portion 82, 82A of the tibial tray 14, 14A is a titanium metal foam. Such a foam may be made as taught in the following U.S. patent applications: U.S. Publication No. 20080199720A1 (U.S. patent application Ser. No. 11/677,140), filed on Feb. 21, 2007 and entitled "Porous Metal Foam Structures And Methods"; U.S. Publication No. US 20100098574A1 (U.S. patent application Ser. No. 12/540,617) entitled "Mixtures For Forming Porous Constructs"; U.S. Publication No. 20090326674 A1 (U.S. patent application Ser. No. 12/487,698) entitled "Open Celled Metal Implants with Roughened Surfaces and Method for Roughening Open Celled Metal Implants;" and U.S. Publication No. 20090292365A1 (U.S. patent application Ser. No. 12/470,397) entitled "Implants with Roughened Surfaces"; the disclosures of all of the above patent applications are incorporated by reference herein in their entireties. The titanium metal powder used to make the porous metal portion

82, 82A may comprise commercially pure titanium powder (such as a titanium powder, 325 mesh (<45 um), produced by a hydride-dehydride process and that meets the ASTM F-1580 standard, available from Phelly Materials, Inc., Bergenfield, N.J., Part No. THD325 for example) or a mix of such a powder with a compatible titanium alloy powder, such as alloy Ti-6Al-4V. This material is advantageous in that it can be sintered to a titanium alloy such as Ti-6Al-4V. It is expected that other grades of commercially pure titanium may be used as well and that other powder metal materials may be available or developed in the future that can provide at least some of the advantages of the present invention; the present invention is not limited to any particular material unless expressly called for in the claims.

Although titanium foam is preferred, some of the advantages of the present invention may be achieved with alternative materials as well. One example of a suitable alternative material is tantalum porous metal, disclosed, for example in U.S. Pat. No. 5,282,861, entitled "Open Cell Tantalum Structures for Cancellous Bone Implants and Cell and Tissue Receptors," the disclosure of which is hereby incorporated by reference herein. Another example of an alternative is a solid metal body made from an implantable metal such as stainless steel, cobalt chrome alloy, titanium, titanium alloy or the like and with a porous coating disposed on both the bone-engaging surface and the surface engaging the polymer portion of the tibial tray. One type of porous coating which may be used as the porous portion 82, 82A of the tibial tray 14, 14A is Porocoat® porous coating which is commercially available from DePuy Orthopaedics of Warsaw, Ind. The porous metal preform 84A may be made using any of the process described in the above-cited patents and patent applications or through any standard process.

To make the tibial tray 14, 14A of the invention, the solid metal portion 80, 80A may be made as a solid metal preform by conventional methods, such as by casting, machining or some combination of casting and machining Such processes may also be used to make a solid metal preform for the femoral component 12. For either the tibial tray 14, 14A or the femoral component 12, the recesses 122, 124, 126, 128, 130, 122A, 124A, 126A, 128A, 130A, and posts or studs 132, 134, 136, 138, 140, 132A, 134A, 136A, 138A, 140A may be machined into the solid metal preforms. For studs of the type illustrated in FIG. 21, threads may be formed in the studs 132, 134, 136, 138, 140 as well. For studs of the type illustrated in FIG. 22, the outer surface of the studs 132A, 134A, 136A, 138A, 140A may be shaped to define a Morse taper post.

It is expected that the articulation and mounting surfaces 18, 20, 26 of the solid metal portions of the femoral and tibial components 12, 14 may be treated to increase the lubricity, such as through Type II hard annodization.

The porous metal portion 82, 82A of the tibial tray 14, 14A and femoral component 12 may be made by molding the desired shape, using the processes described, for example, in U.S. Publication No. 20080199720A1; U.S. patent application Ser. No. 12/540,617 entitled "Mixtures For Forming Porous Constructs". Preforms so made can have, for example, a bulk porosity (or percent open area or void space) of from about 60% to about 85% (preferably about 65% to about 75%) as measured by volume, the forced intrusion of liquid mercury, and cross-section image analysis. This porosity/void space corresponds with a preform having a density of 15-35% (preferably 25-35%) of theoretical density for a similarly sized and shaped solid metal component. It should be understood that the porosity can be a product of various factors in the manufacturing process, such as the size of pore forming agent used. The resultant titanium metal foam may be treated to increase its roughness, such as by etching or blasting, as discussed in more detail below.

The molds used for preparing the porous metal portion 82A may be shaped so that the resultant product defines a single, integral porous metal preform 84A such as that illustrated in FIG. 16. Such a preform can used to make a tibial tray 14A such as that illustrated in FIGS. 6-7. Alternatively, a plurality of molds may be provided to make individual and discrete extensions 30, 32, 34, 36, 38 and an individual and discrete base 85 for the embodiment of FIGS. 4-5 and 8-9. The bores 41, 43, 45, 47, 49, 41A, 43A, 45A, 47A, 49A in these components may be formed as part of the molding process or machined into the finished metal foam construct. For extensions of the type illustrated in FIGS. 5 and 9-12, threads may be formed in the walls defining the bores 41, 43, 45, 47, 49. For extensions of the type illustrated in FIGS. 7, 13-16 and 23, the walls defining the bores 41A, 43A, 45A, 47A, 49A may be tapered to define Morse taper bores.

The porous metal portion 82, 82A of the implant component and the solid metal portion 80, 80A of the implant component may then be assembled. For example, for an implant component of the type illustrated in FIGS. 6-7, the integral preform 84A may be pressed onto the distal surface 120A of the solid metal portion 80A, with the Morse taper studs 132A, 134A, 136A, 138A, 140A of the solid metal portion 80A pushed into the Morse taper bores 41A, 43A, 45A, 47A, 49A of the preform 84A, and with the annular raised portions 29A, 31A, 33A, 35A, 37A of the porous metal preform 84A received in the recesses 122A, 124A, 126A, 128A, 130A surrounding the studs 132A, 134A, 136A, 138A, 140A of the solid metal portion or preform 80A, as shown in FIGS. 7 and 22. The Morse taper frictional connection between the studs and the bores should hold the assembly together until sintering is complete. For an implant component of the type illustrated in FIGS. 4-5, each porous metal extension 30, 32, 34, 36, 38 may be individually assembled with the solid metal base 80 by threading the threaded bore 41, 43, 45, 47, 49 of each porous metal extension 30, 32, 34, 36, 38 onto the threaded stud 132, 134, 136, 138, 140 of the solid metal portion or preform 80 until the annular end of the extension is received in the recess 122, 124, 126, 128 130 surrounding the stud 132, 134, 136, 138 as shown in FIG. 11. This threaded connection between the studs 132, 134, 136, 138 and the bores 41, 43, 45, 47, 49 should hold the assembly together until sintering is complete. It should be understood that the Morse taper connection and threaded connection described above are two examples of complementary structures for connecting the porous metal extensions to the solid metal portion of the tray; those skilled in the art will recognize that other types of connections may be used.

The assembly of the solid metal portion 80, 80A, 81 and the porous metal 82, 82A, 83 portion may then be sintered together to form the final tibial tray 14, 14A or femoral component 12. Sintering may be accomplished utilizing the same temperatures and times used to form the porous metal portion. For example, as disclosed in U.S. Pub. No. 20080199720A1, the assembly may be sintered under the following conditions to form the final implant component: heating at temperatures of from about 2100° F. to about 2700° F. (preferably about 2500° F.) for about 2 hr to about 10 hr (preferably about 3 hr to about 6 hr).

For both the femoral and tibial components, once assembled, the porous metal portion 82, 82A, 83 defines the bone-engaging surfaces 13, 15, 28, 28A of the implant component 12, 14, 14A. In addition, for both the femoral and tibial components, the solid metal portions 80, 80A, 81 contact the bearing 16, both on the mounting side 19 and the articulation side 17.

As mentioned above, in some situations, it may be desirable to treat the porous metal portion 82, 82A, 83 to increase the roughness of the bone-engaging surfaces. The porous metal portion 82, 82A, 83 may be treated through etching or blasting, for example, to increase the roughness of the outer surface, as disclosed, for example in U.S. Pat. Publication No. 20090326674A1 (U.S. patent application Ser. No. 12/487, 698) entitled "Open Celled Metal Implants with Roughened Surfaces and Method for Roughening Open Celled Metal Implants," and U.S. Pat. Publication No. 20090292365A1 (U.S. Pat. App. Ser. No. 12/470,397) entitled "Implants with Roughened Surfaces." Although the etching and blasting techniques disclosed in those patent applications are advantageous for use with titanium metal foams, it should be understood that the techniques disclosed in these patent applications are provided as examples only; the present invention is not limited to roughened porous metal or to any particular roughening technique unless expressly called for in the claims. The disclosures of these patent applications are incorporated by reference herein in their entireties. Such roughening is expected to make the treated surfaces more conducive to bone ingrowth to improve ultimate fixation of the components.

A variety of other techniques are known for treating porous metal implants and may be applied to the present invention. For example, calcium phosphate coatings (such as hydroxyapatite) may be applied to the porous portions of the embodiments of the present invention, with or without additional therapeutic agents, as disclosed in U.S. Pat. Pub. No. 20060257358 entitled "Suspension Of Calcium Phosphate Particulates For Local Delivery Of Therapeutic Agents." Alternatively, electrophoretic deposition of a material such as calcium phosphate may be used.

As disclosed in U.S. patent application Ser. No. 12/470, 397, porous metal samples (both commercially pure titanium and Ti-6Al-4V) were machined in the green state and the static coefficients of friction with polymer bone analogs for the surfaces were found to be 0.52 for commercially pure titanium and 0.65 for Ti-6Al-4V, with standard deviations of 0.1. In contrast, porous metal components of the same materials that were blasted as taught in that patent application had average static coefficients of friction with polymer bone analogs of 0.72-0.89 for commercially pure titanium and 1.09-1.35 for Ti-6Al-4V. As described in that patent application, these tests were performed using a polymer bone analog having a density of about 20 lb/ft3. One example of a bone analog is Cat. No. FR-4520 from General Plastics Manufacturing Co. (Tacoma, Wash.), which is said to be a "rigid, closed-cell polyurethane foam" with a density of 20 lb/ft$^3$. The friction test was performed using a "sled on a plane" method. The "sled" consisted of the 0.75 in×0.75 square metallic matrix samples, whereas each "plane" was a milled sample of Last-A-Foam® 6720 (General Plastics Manufacturing Company, Tacoma, Wash.), a rigid, closed-cell polyurethane foam with a density of 20 lb/ft 3. Each sled was connected to a 250 N load cell by 10 lb monofilament line and pulled at 10 mm/min for 0.8 in. A weight was placed on the sled to create a normal force of 30 N. The static friction coefficient was calculated from the maximum force recorded before the first 0.5 N drop in force.

Profile parameters of the test samples are also provided in U.S. patent application Ser. No. 12/470,397 pursuant to ISO 4287 (1997). As there shown the Pa, Pp, Pt and Pq values (as defined in that patent application) for the samples all at least doubled for the blasted samples as compared to the machined samples with no blasting.

One application of the etching and blasting roughening techniques of the above-identified patent applications is to roughen the porous metal portions 82, 82A, 83 of the tibial tray 14, 14A and femoral component 12. In addition, it may be advantageous to selectively roughen certain surfaces of the porous metal portion 82, 82A, 83 while leaving other surfaces in their as-machined state, with lower roughnesses. Specifically, to facilitate removal of either the tibial tray 14, 14A or the femoral component 12 from the bone in revision surgery, it may be desirable to discourage bone ingrowth at the distal ends 40, 42, 44, 46, 48, 40A, 42A, 44A, 46A, 48A of the tibial extensions and proximal ends 51 of the femoral extensions 39. This may be accomplished by selectively roughening the distal bone-engaging surface 24, 24A of the platform and the outer surfaces of the extensions 30, 32, 34, 36, 38, 30A, 32A, 34A, 36A, 38A at the junctions 60, 62, 66, 69, 60A, 62A, 66A and adjacent surfaces while leaving the ends 40, 42, 44, 46, 48, 40A, 42A, 44A, 46A, 48A opposite the junctions 60, 62, 66, 69, 60A, 62A, 66A (and some adjacent surfaces if desired) in the as-machined state. For example, a tibial tray made according to this aspect of the invention may have a stem 30, 30A and pegs 32, 34, 36, 38, 32A, 34A, 36A, 38A with distal surfaces 40, 42, 44, 46, 48, 40A, 42A, 44A, 46A, 48A having a coefficient of static friction (with a polymer bone analog comprising rigid closed-cell polyurethane foam with a density of about 20 lb/ft$^3$) lesson greater than 0.7; the outer surfaces of these pegs 32, 34, 36, 38, 32A, 34A, 36A, 38A and stem 30, 30A near the junctions 60, 62, 66, 60A, 62A, 66A may have coefficients of static friction (with a polymer bone analog comprising rigid closed-cell polyurethane foam with a density of about 20 lb/ft$^3$) of more than 0.7. For pegs 32A, 34A, 36A, 38A of the type illustrated in FIGS. 7, 12-14 and 16, the flat distal surface 42A, 44A, 46A, 48A may have a lower coefficient of friction; for an extension of the type illustrated in FIGS. 1, 3-5 and 9, all or part of the spheroidal distal end may have a lower coefficient of friction. Similar results are expected to be obtained with selective etching of the extensions. Alternatively, the surfaces of the porous metal portion 82, 82A where bone ingrowth is undesirable may be machined, milled, polished or otherwise smoothed to reduce the roughness and/or porosity of the surface. Machining, milling, polishing or smoothing can be expected to close some or all of the pores and lower the coefficient of friction along the surface. For example, the surfaces where bone ingrowth is undersirable may be machined with a standard carbide tip rotating at a standard speed, such as 600 rpm. Machining may be carried on until the surface is smeared and has a solid rather than porous appearance; about 0.015 inches of material may be removed in this process. It should be understood that a commercial manufacturing process may be run under different parameters. Machining, milling, polishing or smoothing can be accomplished when the component is in the green state, before sintering, after sintering, or both before and after sintering.

Alternatively, pores may be selectively filled with metal. As another alternative, when molding the porous metal portion of the implant or the pegs and stem, or when sintering the solid metal and porous metal portions together, solid metal pieces may be sintered to the free ends of the pegs and stems. Another alternative would include molding a non-porous biocompatible polymer cap to the ends of the extensions; an example of such a polymer is polyetheretherketone (PEEK).

The porosity and roughness of other surfaces may also be modified. Considering the embodiment of FIGS. 1 and 3, for example, there are surfaces of the porous portion 82 that are not intended to engage bone or another part of the implant component. An example of such a surface is exposed peripheral surface 150 of the porous portion 82 of the tibial tray 14. This exposed peripheral surface 150 extends generally perpendicularly from the distal bone-engaging surface 28 to the upper surface 86 of the porous base 85 in the embodiment of FIGS. 1, 3 and 5. At least some of this exposed peripheral surface can be expected to be engaged by soft tissue when implanted. If this exposed peripheral surface is rough, adjacent soft tissue could be irritated when the tray is implanted. Accordingly, it may be preferable to smooth these exposed peripheral surfaces, or any surface that may engage soft tissue instead of bone or another portion of the implant. Any of the methods described above could be used. For example, the exposed peripheral surfaces could be machined with a carbide bit as described above. The coefficient of static friction of such a surface is expected to be no greater than those reported in U.S. patent application Ser. No. 12/470,397 for metal foam samples machined in the green state and not subjected to any roughening treatment (0.52 for commercially pure titanium and 0.65 for Ti-6Al-4V, with standard deviations of 0.1). Profile parameters of the peripheral exposed surfaces are also expected to be no rougher than the Pa, Pp, Pt and Pq values (as defined in U.S. patent application Ser. No. 12/470,397) for the metal foam samples machined in the green state. It is anticipated that the machining parameters could be adjusted to optimize the surface finishes of the peripheral exposed surfaces and distal surfaces 40. The exposed porous metal surfaces perpendicular to the bone-engaging surfaces of the femoral component 12 may be similarly treated.

Figure 31:
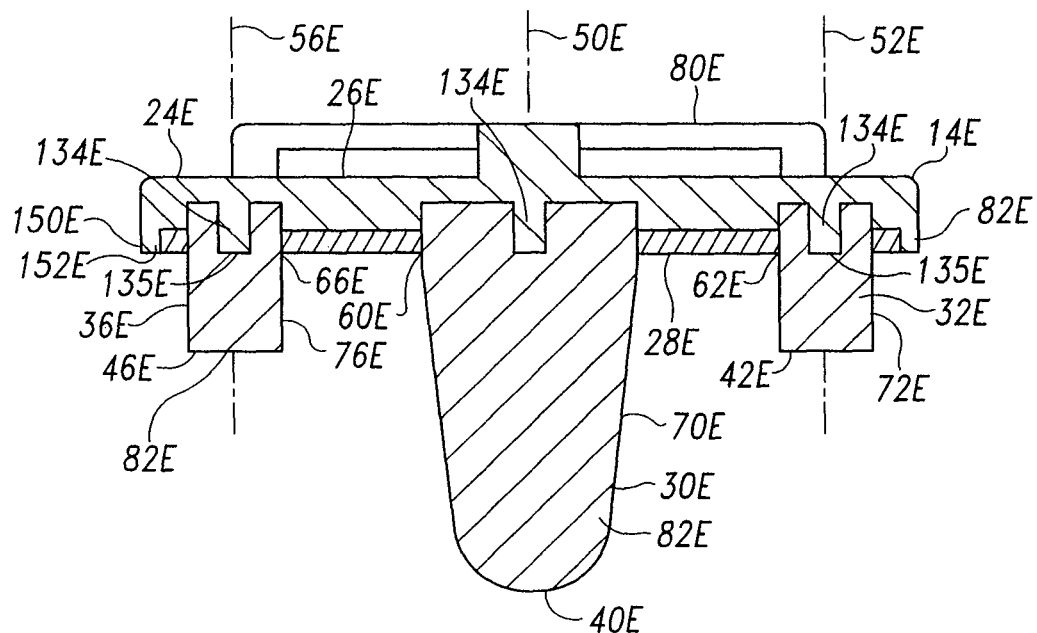
FIG. 31 is a cross-sectional view similar to FIGS. 5, 7 and 28, of an alternative embodiment of a tibial tray that may be used in the present invention

An alternative embodiment of a tibial tray is illustrated in FIG. 31, where the same reference numbers have been used as those used in describing corresponding or similar parts in the embodiments of FIGS. 1 4-7, 11, 18 and 20-23 followed by the letter "E". In this embodiment, the periphery of the solid metal portion 80E includes a rim 152 that extends to the plane of the bone-engaging surface 28E. In this embodiment, the rim 152 defines a pocket in which the porous metal base 85E is received so that the exposed peripheral surface 150E comprises solid metal. In this embodiment, the tibial tray may be made from a base component, such as a cast component, with pockets configured for cemented fixation, and the pockets could be filled with porous metal, such as a titanium foam, and then sintered.

Figure 32:
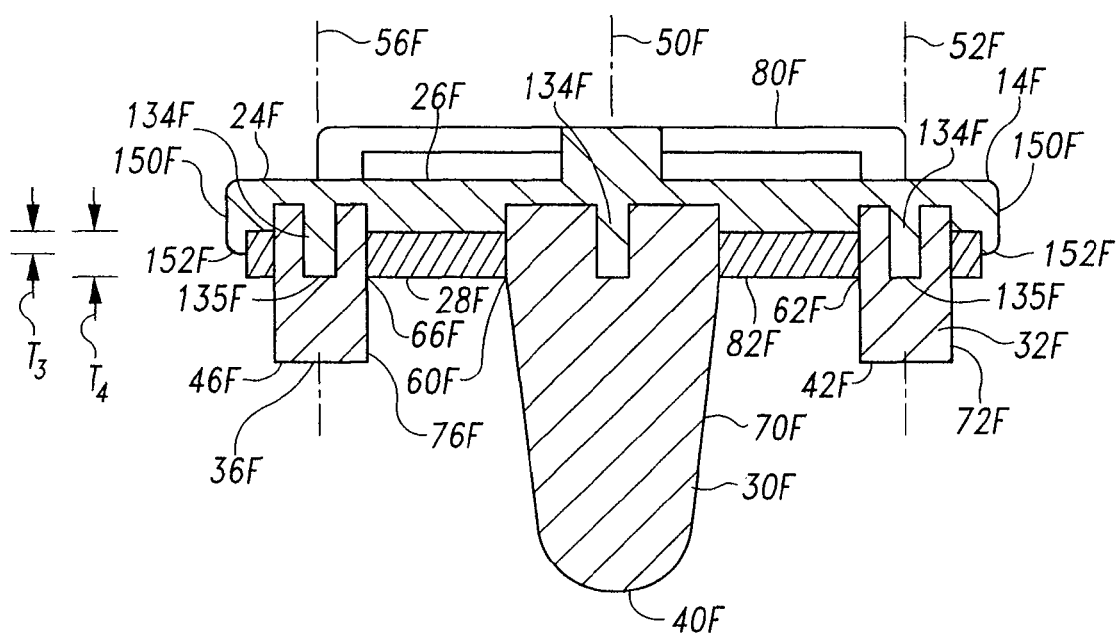
FIG. 32 is a cross-sectional view similar to FIGS. 5, 7, 28 and 31, of an alternative embodiment of a tibial tray that may be used in the present invention.

Another alternative embodiment of a tibial tray is illustrated in FIG. 32, where the same reference numbers have been used as those used in describing corresponding or similar parts in the embodiments of FIGS. 1 4-7, 11, 18, 20-23 and 31 followed by the letter "F". In this embodiment, the periphery of the solid metal portion 80E includes a rim 152F that extends to a plane above the plane of the bone-engaging surface 28F. In this embodiment, the rim 152F defines a pocket in which a portion of the porous metal base 85F is received. In this embodiment, the porous metal base 85F is recessed from the periphery of the tibial tray to eliminate contact between the porous metal and soft tissue. Thus, the exposed peripheral surface 150F comprises solid metal. In this embodiment, the tibial tray may be made from a base component, such as a cast component, with pockets configured for cemented fixation, and the pockets could be filled with porous metal, such as a titanium foam, and then sintered. The pockets defined by the rim 152F have a depth shown at $T_3$ in FIG. 32, and the porous metal base 85F has a thickness shown as $T_4$ in FIG. 32. $T_4$ is greater than $T_3$ to ensure that the bone-engaging surface 28F stands proud to thereby ensure that the surface 28F fully engages and transfers load to the underlying bone.

Bone loss on the proximal tibia or distal femur can make it difficult to properly position and support the tibial component 14, 14A or femoral component 12 of the implant system 10 on the bone surface. The prior art has addressed this problem through the use of wedges or augments. Generally, the wedge or augment is placed between part of the bone-engaging surface of the implant component and part of the bone to support part of the implant component on the bone by augmenting part of the bone.

Due in part to the fact that the size, shape and anatomy of virtually every patient is different, and the variability in the location and amount of bone loss on the proximal tibia, an extensive number of a variety of wedges and augments have been made available to the orthopedic surgeon. For example, a typical surgical kit will include tibial wedges of different thicknesses and different configurations for use on either the medial or the lateral sides of the tibial.

In the present invention, the prosthetic knee system or kit 10 may include wedges or augments for both the femoral and tibial sides of the system. These augments may comprise porous metal, and more particularly, a porous metal foam of the same material and made under the same conditions as those discussed above for the porous metal portions 82, 82A, 83 of the tibial trays 14, 14A and femoral components 12.

For the femoral side, augments may have features such as those disclosed in the following U.S. Pat. Nos. 6,005,018 and 5,984,969, which are incorporated by reference herein in their entireties. For the tibial side, augments may have features such as those disclosed in U.S. Pat. Nos. 7,175,665 and 5,019, 103, which are incorporated by reference herein in their entireties.

Figure 24:
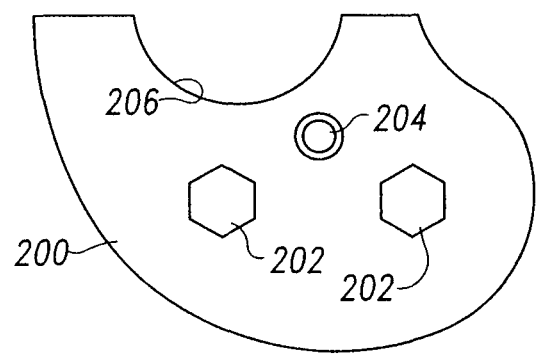
FIG. 24 is a bottom plan view of a tibial augment that may be used with the present invention.
Figure 25:
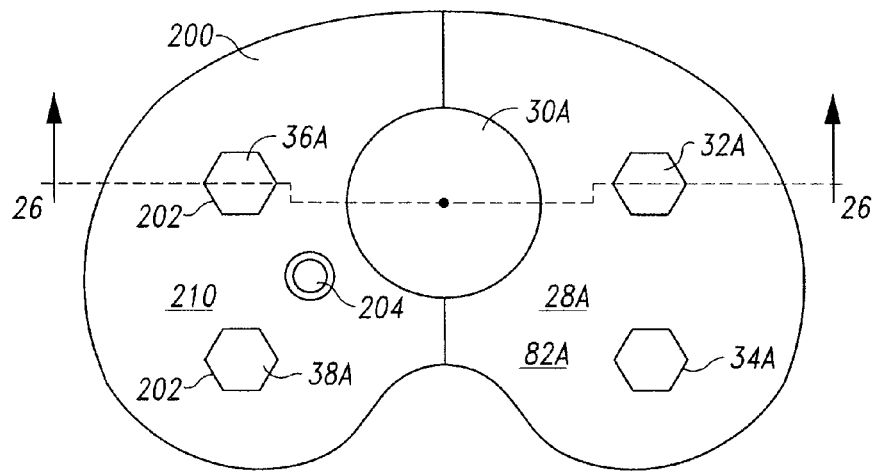
FIG. 25 is a bottom plan view of the tibial augment of FIG. 24 assembled with a tibial tray similar to that shown in FIGS. 6-7.
Figure 26:
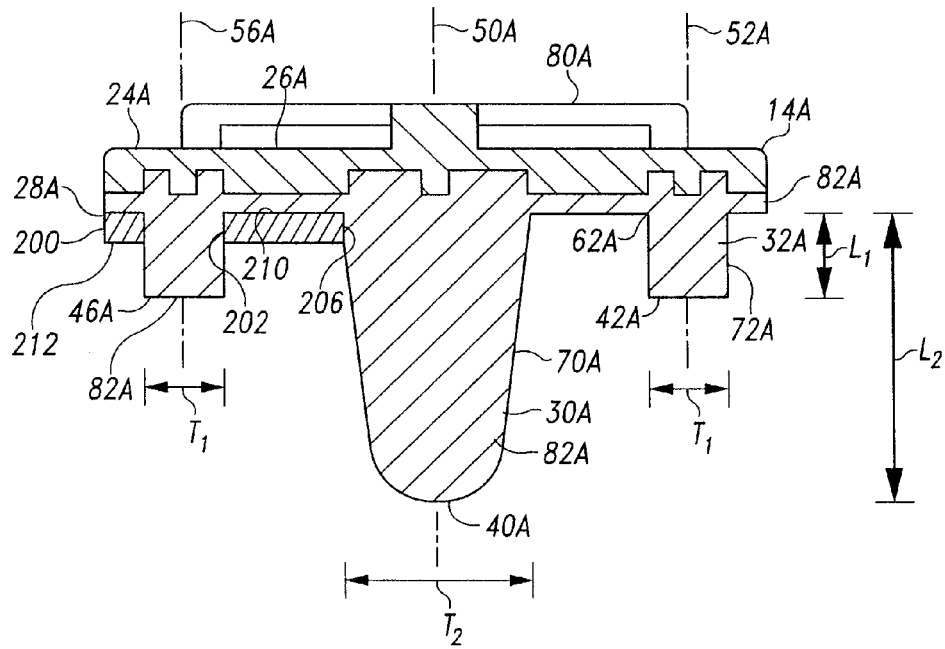
FIG. 26 is a cross sectional view of the assembly of FIG. 25, taken along line 26-26 of FIG. 25, as viewed in the direction of the arrows.

An illustrative tibial augment is shown in FIG. 24 at 200. The illustrated tibial augment 200 is made of porous metal across its entire length, width and thickness. The augment 200 includes through-bores 202 sized and shaped to receive portions of pegs or extensions (such as pegs 32, 34, 36, 38, 32A, 34A, 36A, 38A) that may be present, and may be mounted to the porous metal portion 82, 82A of the tibial tray as illustrated in FIGS. 25-26. Frictional engagement of the augment and the pegs or extensions and the porous metal portion of the tray may be sufficient to fix the augment to the tray; otherwise, the augment 200 may include additional through-bores sized and shaped to receive screws (not shown) for fixing the augment 200 to the tibial tray 14, 14A; an illustrative through bore is shown at 204 in FIGS. 24-25. The augment 200 may also include a recess such as recess 206 to accommodate any stem (such as stem 30, 30A) on the tibial tray 14. Complementary blind bores may be provided in the tibial tray to receive parts of the screws. The bores in the tibial tray may be threaded, and may be provided in the porous metal portion 82, 82A or may extend through the porous metal portion 82, 82A and into the solid metal portion 80, 80A. The surfaces defining the through-bores 202, 204 in the augments may be smooth (i.e., non-threaded) and the through-bores 204 for the screws may have top and bottom countersinks so that the augment may be used on either the medial or lateral side, as disclosed in U.S. Pat. No. 7,175,665. As shown in FIG. 26, when the augment is mounted on the tibial tray 14A, one surface 210 of the augment bears against distal surface 28A of the porous metal portion 82A of the tray 14A and the opposite surface 212 of the augment 200 becomes the bone-engaging surface of this side of the tibial tray 14A.

The augment 200 may comprise a porous metal foam. For example, the augment 200 may be made according to the processes disclosed in the following U.S. patent applications: U.S. Publication No. 20080199720A1 (U.S. Ser. No. 11/677,140), filed on Feb. 21, 2007 and entitled "Porous Metal Foam Structures And Methods"; U.S. patent application Ser. No. 12/540,617 (Docket No. DEP6171USNP) entitled "Mixtures For Forming Porous Constructs"; U.S. patent application Ser. No. 12/487,698 (Docket No. DEP5922USNP) entitled "Open Celled Metal Implants with Roughened Surfaces and Method for Roughening Open Celled Metal Implants;" and U.S. patent application Ser. No. 12/470,397 (Docket No. DEP6089USNP) entitled "Implants with Roughened Surfaces." Exposed peripheral surfaces of the augments, such as surface 250 in FIGS. 25 and 26, may be treated to smooth the exposed peripheral surface 250. The smoothing treatment may comprise, for example, machining as discussed above; alternatively or in addition, the surface 250 may be masked during any process used to roughed other surfaces of the augment.

To use the system of the present invention, the surgeon would prepare the distal femur and proximal tibia to receive the bone implants 12, 14, 14A using conventional techniques and implant the tibial tray and femoral component using conventional techniques for cementless components. The tibial bearing 16 is typically assembled with the tibial tray 14, 14A after the tray 14, 14A has been implanted.

After implantation, it is anticipated that bone will grow into the porous metal portion 82, 82A of the tibial tray 14, 14A and porous metal portion 83 of the femoral component 12, including the pegs 32, 34, 36, 38, 39, 32A, 34A, 36A, 38A and stem 30, 30A. If the pegs and stem are made with smoother free ends 40, 42, 44, 46, 48, 51, 40A, 42A, 44A, 46A bone will not, however, grow or grow as vigorously into the smoother free ends. Thus, it is anticipated that there will be bone ingrowth into the distal surface 28, 28A of the tibial platform 24, 24A and porous metal portion 83 of the femoral component 12. In addition, bone ingrowth is also anticipated into the exterior surfaces 70, 72, 76, 79, 70A, 72A, 76A of the extensions 30, 32, 34, 36, 38, 39, 30A, 32A, 34A, 36A, 38A adjacent to the distal surface 28 of the tibial platform 24 and porous metal portion 83 of the femoral component 12 as well as at the junctions 60, 62, 66, 69, 60A, 62A, 66A. Radial pressure along the proximal exterior surfaces 70, 72, 76, 79, 70A, 72A, 76A is expected to be uniform, to stimulate bone ingrowth in all directions on the stem and pegs 30, 32, 34, 36, 38, 39, 30A, 32A, 34A, 36A, 38A. If the ends 40, 42, 44, 46, 48, 51, 40A, 42A, 44A, 46A of the pegs and stem are smoother (or comprise solid material) than the rest of the porous metal portion, bone is not expected to grow or to grow as vigorously into the smoother exposed exterior surfaces at the distal ends 40, 42, 44, 46, 48, 51, 40A, 42A, 44A, 46A of the extensions 30, 32, 34, 36, 38, 39, 30A, 32A, 34A, 36A, 38A.

The extensions 30, 32, 34, 36, 38, 39, 30A, 32A, 34A, 36A, 38A stabilize the implant component 12, 14, 14A when implanted in a bone of a patient. The central stem 30, 30A provides stability against lift off for the tibial tray. The pegs 32, 34, 36, 38, 32A, 34A, 36A, 38A surrounding the central stem 30, 30A and pegs 39 of the femoral component 12 provide stability by reducing shear and micromotion, especially after bone ingrowth has occurred.

If the exposed peripheral surfaces 150, 250 of the implant components are smooth, no soft tissue irritation should occur after the components are implanted.

If it becomes necessary to remove the tibial tray 14, 14A or femoral component 12, the surgeon may cut along the distal bone-engaging surface 28, 28A of the tibial tray platform 24, 24A (or along the distal surface 212 of an augment 200) to sever the connection between the patient's bone and the tibial tray platform 24, 24A at the interface. If the pegs 32, 34, 36, 38, 39, 32A, 34A, 36A, 38A and stem 30, 30A consist of porous metal foam across their entire thicknesses $T_1$ and $T_2$, the surgeon may also cut through all of the extensions 30, 32, 34, 36, 38, 39, 30A, 32A, 34A, 36A, 38A at the junctures 60, 62, 66, 69, 60A, 62A, 66A of the extensions 30, 32, 34, 36, 38, 39, 30A, 32A, 34A, 36A, 38A and the distal surface 28, 28A of the tibial platform 24, 24A and bone-engaging surfaces 13, 15 of the femoral component 12 using a bone saw and easily remove the tibial platform 24, 24A and femoral component 12. Such a result is generally not possible with pegs and stems made of solid titanium or cobalt chrome alloy, since bone saws cannot generally cut through solid metal. To remove the extensions 30, 32, 34, 36, 38, 39, 30A, 32A, 34A, 36A, 38A, the surgeon may then cut around the outer perimeter of each extension 30, 32, 34, 36, 38, 39, 30A, 32A, 34A, 36A, 38A to sever the connection between the bone and the extensions 30, 32, 34, 36, 38, 39, 30A, 32A, 34A, 36A, 38A. Such cuts around the perimeters may be made, for example, through use of a trephine saw. Each extension 30, 32, 34, 36, 38, 39, 30A, 32A, 34A, 36A, 38A may then be readily removed. Notably, if the free ends of the extensions are smooth, little or no bone ingrowth will have occurred at the ends of the extensions, so the removal of the stem and pegs should be made easier.

As indicated above, sawing through the stem and pegs 30, 32, 34, 36, 38, 39, 30A, 32A, 34A, 36A, 38A, 30D, 32D, 36D, 30E, 32E, 36E is made easier if the stem and pegs at the junctions 60, 62, 66, 69, 60A, 62A, 66A, 60D, 62D, 66D, 60E, 62E, 66E consist of porous metal rather than solid metal. Generally, it is believed that the stem and pegs may be cut through transversely with a standard surgical saw if the material is 25-35% of theoretical density. Notably, in the illustrated embodiments, the titanium alloy studs 132, 134, 136, 138, 140, 132A, 134A, 136A, 138A, 140A, 134D, 134E do not extend beyond the plane of bone-engaging surface 28, 28A, 28D, 28E; therefore, in cutting through the extensions 30, 32, 34, 36, 38, 39, 30A, 32A, 34A, 36A, 38A, 30D, 32D, 36D, 30E, 32E, 36E, the surgeon need not cut through the solid metal studs 132, 134, 136, 138, 140, 132A, 134A, 136A, 138A, 140A, 34D, 134E.

It is anticipated that a standard surgical saw could cut through a somewhat more dense material. In addition, it is anticipated that a standard surgical saw could cut through a composite of materials, such as a small diameter central core of solid metal (e.g. titanium alloy) surrounded by a porous metal foam (e.g. commercially pure titanium). Accordingly, although for purposes of ease of removal, it is preferred that the entire thicknesses of the extensions be porous metal at the junctions, other considerations may call for a composite of materials to be used.

Thus, the present invention provides a knee prosthesis with a tibial implant component and femoral component suitable for optimized cementless fixation. Moreover, the implant components can be readily removed from the bone in revision surgery to conserve native bone.

Figure 27:
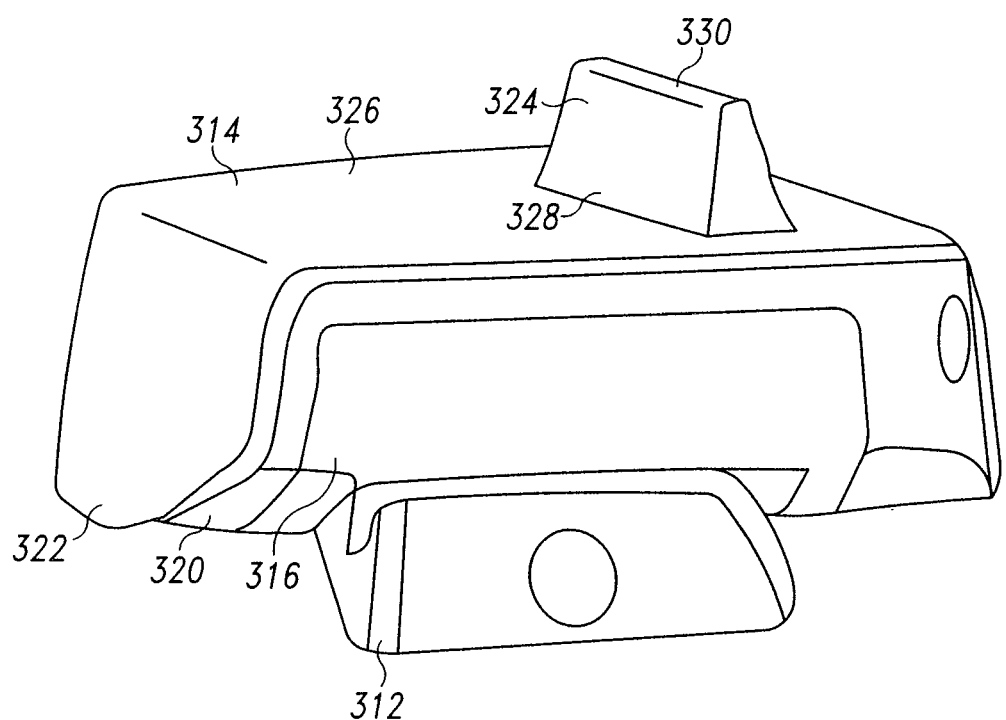
FIG. 27 is a perspective view of an ankle prosthesis embodying the principles of the present invention.

It will be appreciated that the principles of the present invention are expected to be applicable to other joint prostheses as well. An example of such a joint prosthesis is shown in FIG. 27. The joint prosthesis of FIG. 27 is an ankle prosthesis. The illustrated ankle prosthesis comprises a talar component 312, a composite distal tibial component 314 and a bearing 316. In the illustrated embodiment, the composite distal tibial component 314 comprises a distal solid metal portion 320 and a proximal porous metal portion 322, sintered together as described above for the knee prosthesis 10. As in the knee prosthesis 10, the solid metal portion 320 and the bearing may have mounting surfaces with complementary locking features (not shown) so that the bearing 316 can be fixed to the solid metal portion 320 of the tibial component 314. The illustrated distal tibial component 314 has a proximal extension 324 extending proximally from the bone-engaging surface 326 of the tibial component 314. The proximal extension 324 may provide porous metal outer surfaces for engaging the bone or the distal portion 328 may comprise porous metal and the proximal portion 330 comprise porous metal with a porosity or reduced coefficient of static friction as described above. A similar extension could be provided in the talar component if desired.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, the number and configurations of the extensions may be varied. For a tibial tray, for example, the tray could include pegs but no central stem. Although the illustrated tibial trays have four pegs, fewer pegs may be acceptable.

Other variations are possible as well. For example, the extensions 30, 32, 34, 36, 38, 39, 30A, 32A, 34A, 36A, 38A, 30D, 32D, 36D, 30E, 32E, 36E could be made as modular components to be assembled with a base plate intraoperatively if desired. The base plate could comprise a porous preform like that shown in FIG. 8 at 85 sintered to a solid metal portion such as that shown at 80 in FIG. 5. The threaded and Morse taper connections described above should be sufficient to hold the components together without sintering, particularly if the studs are longer, as shown in the embodiment of FIGS. 28-30. The extensions and base plate may be provided in a kit form, with the base plate and extensions being discrete components as shown in FIGS. 8-9 and 17-20; the extensions in the kit could have differing properties, such as size or surface finish, and the surgeon may chose the most appropriate extension for the particular patient intraoperatively. For example, a set of extensions could be provided with porous distal ends and a second set of extensions could be provided with smooth distal ends to accommodate surgeon preference.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

We claim:

1. A joint prosthesis comprising:
    a first component having an articulation surface, a solid metal portion, a porous metal portion an opposite bone-engaging surface that is part of the porous metal portion;
    a bearing having an articulation surface shaped to bear against the articulation surface of the first component and an opposite surface; and
    a second component having a mounting surface and an opposite bone-engaging surface;
    wherein the first component has a central sagittal plane and includes a plurality of recesses and a plurality of spaced studs, each stud being received within one recess and having an end, the recesses and studs being spaced from the central sagittal plane of the implant component and being part of the solid metal portion;
    a plurality of extensions, each extension mounted on one stud and extending out from the bone-engaging surface to an end, each extension having an outer surface between the end and the bone-engaging surface, a part of each extension being received in one recess;
    wherein:
    the porous metal portion and extension comprise a titanium metal foam and the solid metal portion comprises a titanium alloy;
    the extensions and the porous metal portion meet at junctions comprising titanium metal foam;
    the porous metal portion, solid metal portion and extensions are bonded together through sintering;
    the junctions lie in a plane; and
    the ends of the studs do not extend beyond the plane of the junctions.

2. The joint prosthesis of claim 1 wherein each stud defines a Morse taper post and wherein each extension includes a Morse taper bore engaging the stud.

3. The joint prosthesis of claim 1 wherein the joint prosthesis is a knee prosthesis, the first component comprises a distal femoral component and the second component comprises a proximal tibial tray.

4. The joint prosthesis of claim 1 wherein the joint prosthesis is an ankle prosthesis and the first component comprises a distal tibial component.

5. A joint prosthesis comprising:
    a first component having an articulation surface and an opposite bone-engaging surface;
    a bearing having an articulation surface shaped to bear against the articulation surface of the first component and an opposite surface; and
    a second component having a solid metal portion, a porous metal portion, a mounting surface and an opposite bone-engaging surface that is part of the porous metal portion;
    wherein the second component has a central sagittal plane and includes a plurality of recesses and a plurality of spaced studs, each stud being received within one recess and having an end, the recesses and studs being spaced from the central sagittal plane of the implant component and being part of the solid metal portion;
    a plurality of extensions, each extension mounted on one stud and extending out from the bone-engaging surface to an end, each extension having an outer surface between the end and the bone-engaging surface, a part of each extension being received in one recess;
    wherein:
    the porous metal portion and extension comprise a titanium metal foam and the solid metal portion comprises a titanium alloy;
    the extensions and the porous metal portion meet at junctions comprising titanium metal foam;
    the porous metal portion, solid metal portion and extensions are bonded together through sintering;
    the junctions lie in a plane; and
    the ends of the studs do not extend beyond the plane of the junctions.

6. The joint prosthesis of claim 5 wherein the joint prosthesis is a knee prosthesis, the first component comprises a distal femoral component and the second component comprises a proximal tibial tray.

* * * * *